(12) United States Patent
Youd et al.

(10) Patent No.: US 11,375,965 B2
(45) Date of Patent: Jul. 5, 2022

(54) STERILE BARRIERS FOR MEDICAL DEVICES

(71) Applicant: Turner Imaging Systems, Inc., Orem, UT (US)

(72) Inventors: Thomas L. Youd, Salt Lake City, UT (US); Douglas P. Hansen, Spanish Fork, UT (US)

(73) Assignee: Turner Imaging Systems, Inc., Orem, UT (US)

(*) Notice: Subject to any disclaimer, the term of this patent is extended or adjusted under 35 U.S.C. 154(b) by 0 days.

(21) Appl. No.: 16/671,493

(22) Filed: Nov. 1, 2019

(65) Prior Publication Data
US 2021/0128091 A1    May 6, 2021

(51) Int. Cl.
*H05G 1/02* (2006.01)
*A61B 6/00* (2006.01)
(Continued)

(52) U.S. Cl.
CPC .......... *A61B 6/4423* (2013.01); *A61B 6/4405* (2013.01); *A61B 6/4441* (2013.01);
(Continued)

(58) Field of Classification Search
CPC ..... A61B 6/4441; A61B 6/102; A61B 6/4447; A61B 6/4423; A61B 6/4464; A61B 6/4405; A61B 6/4411; A61B 6/035; A61B 6/0407; A61B 6/107; A61B 6/487; A61B 2046/205; A61B 46/10; A61B 46/20; A61B 46/27; A61B 46/40; A61B 5/0064; A61B 5/1114; A61B 6/00; A61B 6/032; A61B 34/25; A61B 2090/365; A61B 2034/107; A61B 2090/3966; A61B 6/0492;
(Continued)

(56) References Cited

U.S. PATENT DOCUMENTS

| 5,534,346 A | 7/1996 | Robinson |
| 6,285,902 B1 | 9/2001 | Kienzle, III et al. |

(Continued)

FOREIGN PATENT DOCUMENTS

| WO | 1997017035 A1 | 5/1997 |
| WO | 2015094423 A1 | 6/2015 |

*Primary Examiner* — Irakli Kiknadze
(74) *Attorney, Agent, or Firm* — Kenneth E. Horton; Barnes & Thornburg LLP

(57) ABSTRACT

Sterile barriers or sterile drapes that can be used with medical devices, including hand-held or self-supported X-ray equipment, are described in this application. In particular, this application describes sterile drapes that can be used with a medical device, the drape comprising a closed end portion, a middle portion with a size sufficient to enclose a part of the medical device being used near a patient, and an open end portion, the end portion configured to be closed by a user once the middle portion encloses the part of the medical device being used near a patient, wherein the sterile drape creates a sterile barrier around substantially the entire medical device once the open end is closed. Using the sterile drape allows the medical device, such as a hand-held or self-supported X-ray device, to be used in a medical procedure that requires a sterile field near the patient without disrupting that sterile field. Other embodiments are described.

18 Claims, 20 Drawing Sheets

(51) Int. Cl.
*A61B 46/10* (2016.01)
*G21F 3/00* (2006.01)
*A61B 46/00* (2016.01)

(52) U.S. Cl.
CPC .............. *A61B 46/10* (2016.02); *A61B 46/40* (2016.02); *G21F 3/00* (2013.01)

(58) Field of Classification Search
CPC ........... A61B 2017/00203; A61B 2017/00212; A61B 2017/00216; A61B 2034/2065; A61B 2034/254; A61B 2050/0065; A61B 2050/314; A61B 2090/372; A61B 2090/502; A61B 34/10; A61B 34/20; A61B 46/23; A61B 6/462; A61B 19/081; A61B 19/088; A61B 6/4233; A61B 6/4488; A61B 6/463; A61B 6/467; A61B 6/469; A61B 6/547; A61B 1/00144; A61B 1/00; A61B 1/0149; A61B 34/30; A61B 2017/00477; A61B 1/04; A61B 2034/301; A61B 90/50; A61B 90/20; A61B 6/5235; A61B 90/39; A61B 90/11; A61B 17/1757; A61B 90/90; A61B 17/88; A61B 17/1739; A61B 17/7055; A61B 90/36; A61B 6/4452; A61B 6/447; A61N 2005/1089; A61N 2005/1094; A61N 5/1077; G06T 19/006; G06T 2200/24; G06T 2207/10116; G06T 2207/30008; G06T 7/0012; G06T 7/74; G06T 11/00; G06T 11/60; A61G 10/005; A61G 12/008; A61G 13/0054; A61G 13/101; A61G 13/107; A61G 13/108; A61G 13/121; A61G 13/128; A61G 1/01; A61G 1/013; A61H 31/006; G21F 3/00; G21F 3/02; G21F 1/01; G21F 9/001; H01B 3/441

USPC ........................................................ 378/193
See application file for complete search history.

(56) References Cited

U.S. PATENT DOCUMENTS

| | | | |
|---|---|---|---|
| 6,468,611 B1 | 10/2002 | Haskin | |
| 6,649,236 B2 | 11/2003 | Haskin | |
| 7,706,505 B2 | 4/2010 | Tachikawa | |
| 8,225,495 B2 | 7/2012 | Dehler | |
| 8,286,637 B2 | 10/2012 | Kaska | |
| 8,746,252 B2 | 6/2014 | McGrogan et al. | |
| 9,016,282 B2 | 4/2015 | Grajek et al. | |
| 9,161,816 B2 | 10/2015 | Ball et al. | |
| 9,295,521 B2 | 3/2016 | Pack et al. | |
| 9,855,178 B2 | 1/2018 | Rogers | |
| 2004/0047734 A1 | 3/2004 | Nilson | |
| 2006/0076024 A1* | 4/2006 | Duarte | A61B 46/00 128/849 |
| 2008/0020332 A1* | 1/2008 | Lavenda | A61B 6/4488 430/495.1 |
| 2010/0028397 A1* | 2/2010 | Wooley | A01N 25/34 424/411 |
| 2013/0025605 A1 | 1/2013 | Ball et al. | |
| 2013/0240402 A1* | 9/2013 | Campista | B32B 7/12 206/525 |
| 2015/0124941 A1* | 5/2015 | Arterson | A61B 6/4441 378/204 |
| 2015/0173836 A1* | 6/2015 | Pack | A61B 6/10 378/198 |
| 2015/0366618 A1* | 12/2015 | Higuchi | A61B 90/50 359/510 |
| 2016/0166323 A1* | 6/2016 | Tylka | A61B 46/00 128/852 |
| 2018/0108447 A1 | 4/2018 | Turner et al. | |
| 2018/0214228 A1* | 8/2018 | Toure | A61B 46/10 |
| 2019/0247135 A1* | 8/2019 | McAlister | A61B 46/20 |

\* cited by examiner

STERILE BARRIERS FOR MEDICAL DEVICES

FIELD

This application relates generally to medical devices and particularly x-ray equipment used in medical applications. More specifically, this application relates to sterile barriers that can be used with medical devices, comprising hand-held—including hand-portable and hand-operable—and self-supported X-ray equipment.

BACKGROUND

X-ray imaging systems typically contain an X-ray source and an X-ray detector. X-rays are emitted from the source and impinge on the X-ray detector to provide an X-ray image of the object or objects that are placed between the X-ray source and the detector. The X-ray detector is often an image intensifier or even a flat panel digital detector. In some configurations, these devices contain a C-arm assembly with the source and detector on opposite ends of the "C" arm of the assembly. The C-arm assembly can move through continuous rotation angles relative to the object in order to acquire images from multiple orientations.

Historically, X-ray imaging systems have been physically large devices because the physics of generating an x-ray photon required tens of thousands of volts and the practical means of generating such voltages with any appreciable current required large transformers and related devices. The X-ray source accelerated electrons through the potential difference and then directed them against a metallic anode to generate Bremsstrahlung radiation that could be directed to a detector such as film or another device. The x-ray source was shielded with lead as well as a large air-gap (meaning an appreciable distance in air) to ensure that unintentional irradiation of individuals did not occur. All of these details led to a large device.

Another factor that drove the size of historic x-ray devices was the low photon efficiency of the x-ray detector, which was initially a film. In order to get a useful image with sufficient contrast, a relatively large x-ray flux was required. This again directed the historic X-ray source towards a larger physical size because it is easier to increase the irradiated x-ray power for a larger X-ray source.

Of course, a large physical size meant that historic or conventional X-ray imaging systems have limited mobility since they are supported by a gantry that is secured to a floor, wall, or ceiling and work around a fixed table or other location where the patient can be placed for imaging.

More recently, advances in x-ray detector technology has enabled the introduction of electronic image detection with higher photon efficiencies and reduced X-ray source power requirements. This has enabled the introduction of a smaller class of mobile X-ray imaging systems that are supported on a mobile base (on wheels) so they can be used in a variety of clinical environments and move from room to room. These systems are now common in the radiology and surgery departments of a medical facility such as a hospital.

The latest advances in x-ray sources and x-ray detectors have enabled the introduction of a new class of X-ray imaging devices that are small enough to be held or carried by hand and to even be operated while hand-held. The introduction of a hand-held and hand-operable x-ray imaging system changes the way in which x-ray systems can be used in medicine, and introduces new issues and concerns about how they can be rendered sterile for use in surgery and for use in other medical procedures.

SUMMARY

This application relates generally to sterile barriers that can be used with medical devices, including hand-held or self-supported X-ray equipment. In particular, this application describes sterile drapes that can be used with a medical device, the drape comprising a closed end portion, a middle portion with a size sufficient to enclose a part of the medical device being used near a patient, and an open end portion, the end portion configured to be closed by a user once the middle portion encloses the part of the medical device being used near a patient, wherein the sterile drape creates a sterile barrier around substantially the entire medical device once the open end is closed. Using the sterile drape allows the medical device, such as a hand-held or self-supported X-ray device, to be used in a medical procedure that requires a sterile field near the patient without disrupting that sterile field.

BRIEF DESCRIPTION OF THE DRAWINGS

The following description can be better understood in light of the Figures which show various embodiments and configurations of the sterile drapes that can be used with X-ray equipment used for medical applications.

Figure 1A:
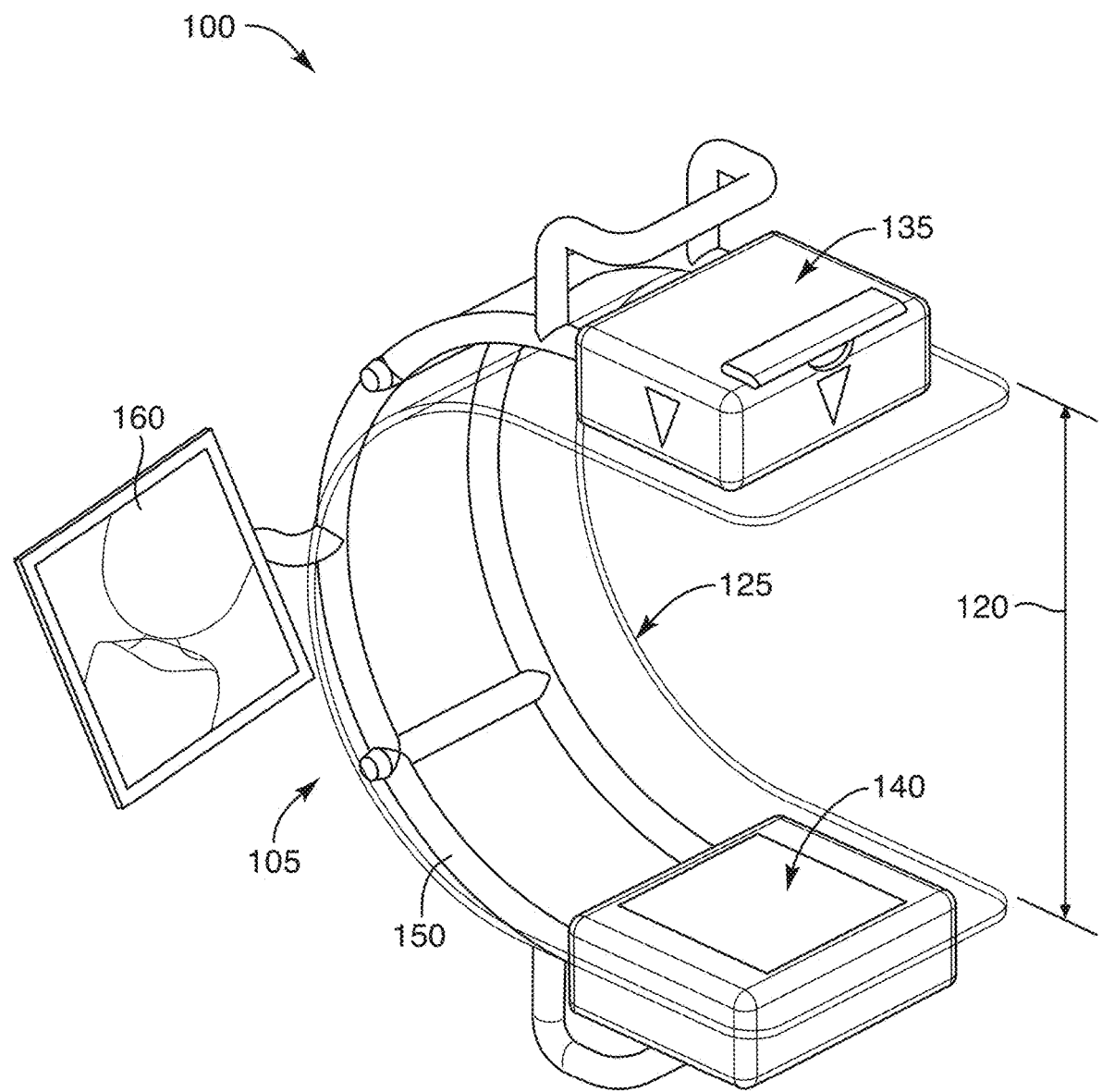
FIGS. 1A and 1B shows a view of some embodiments of small, hand-held X-ray devices.

Together with the following description, the Figures demonstrate and explain the principles of the structures, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices.

DETAILED DESCRIPTION

The following description supplies specific details in order to provide a thorough understanding. Nevertheless, the skilled artisan will understand that the sterile drapes that are described and the way they are employed with the associated X-ray devices can be implemented and used without employing these specific details. Indeed, the described systems and methods for fabricating, applying, and using sterile drapes with hand-held X-ray devices can be placed into practice by modifying the described systems and methods and can be used in conjunction with any other apparatus and techniques conventionally used in the industry. For example, while the description below focuses on hand-held C-arm x-ray devices, other X-ray imaging arms and x-ray devices can be used, including U-arms or portable x-ray devices with separate detectors that are configured to approximate the C-arm configuration. Indeed, the sterile drapes can be used with self-supported x-ray equipment. As well, the sterile drapes can be used with other medical devices where a sterile field needs to be maintained, such as ultrasound equipment and CT scanners.

In addition, as the terms on, disposed on, attached to, connected to, or coupled to, etc. are used herein, one object (e.g., a material, element, structure, member, etc.) can be on, disposed on, attached to, connected to, or coupled to another object—regardless of whether the one object is directly on, attached, connected, or coupled to the other object or whether there are one or more intervening objects between the one object and the other object. Also, directions (e.g., on top of, below, above, top, bottom, side, up, down, under, over, upper, lower, lateral, orbital, horizontal, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more.

Figure 1B:
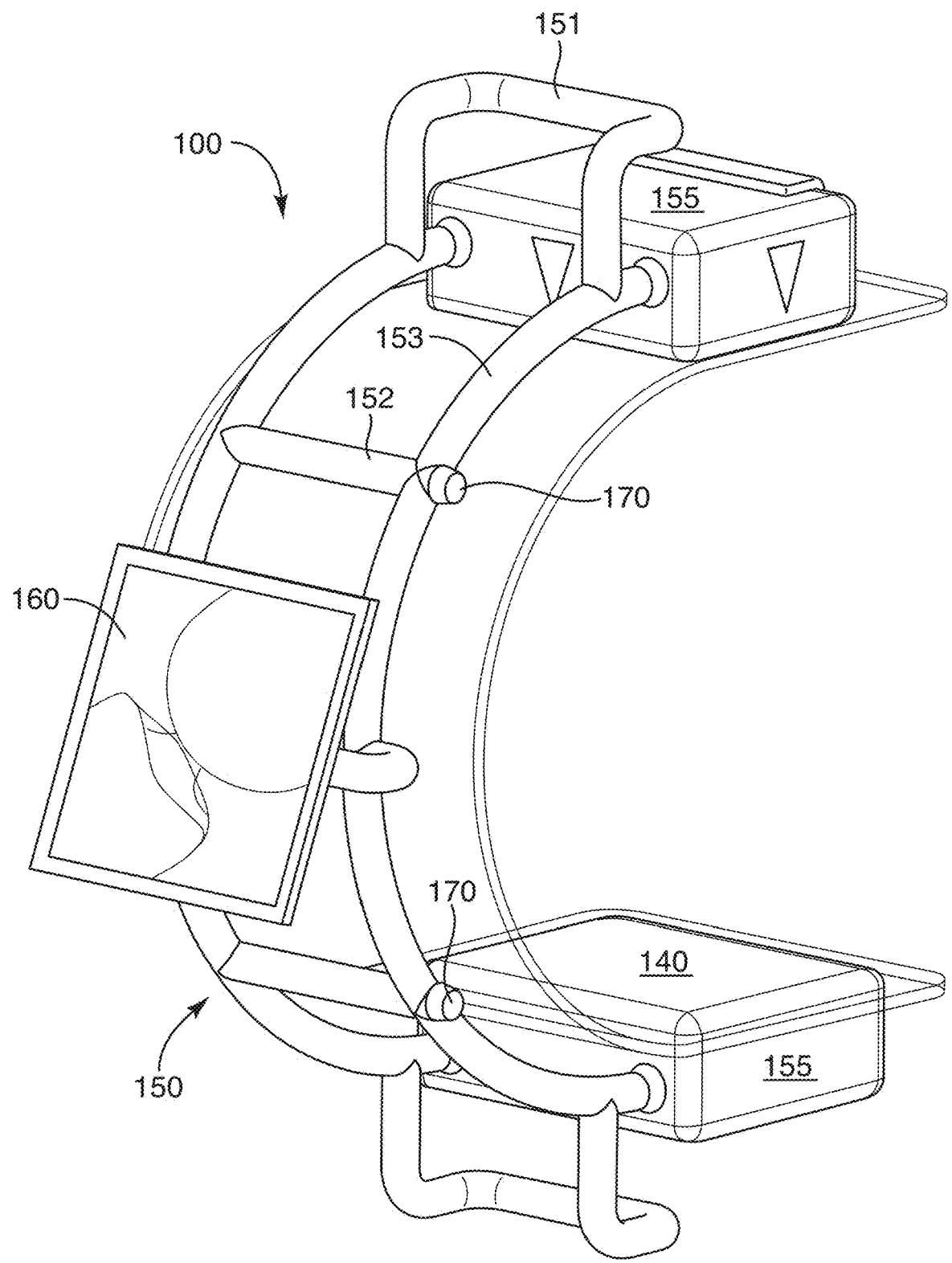

FIGS. 1A and 1B show some embodiments of the hand-held and portable X-ray devices 100. The X-ray devices 100 contain an imaging arm (or support arm) that allows the system to be used to take X-ray images of a portion of a patient's body or any other object capable of being analyzed by x-rays, including animals, industrial components such as electronic circuit boards, containers to be inspected, and/or passenger luggage. In some configurations, the imaging arm is substantially shaped like the letter "C" and is therefore referred to as a C-shaped support arm (or C-arm) 105. The C-arm has any size that can be held and operated by hand when in use, as seen in FIG. 1A or 1B. In some configurations, the x-ray devices 100 can be hand-held so they can be carried by hand and/or operated by hand.

The C-arm 105 can contain any X-ray source 135 and X-ray detector 140 that allow the X-ray system 100 to take X-ray images. The X-ray source 135 can contain any source that generates and emits X-rays, including a standard stationary anode X-ray source, a micro-focus x-ray source, a rotating anode x-ray source, and/or a fluoroscopic X-ray source. In some embodiments, the x-ray source 135 can operate with about 40 to about 90 kV and from about 1 to about 10 mA. In other embodiments, the x-ray source can operate with about 70 KV to about 120 KV and from 1 to about 15 mA. In still other embodiments, the x-ray source can operate with about 75 kV and about 2 mA. In some configurations, the X-ray source and x-ray detector can be made modular so that different sizes and types of X-ray sources and x-ray detectors can be used in the x-ray device 100.

The X-ray detector 140 can contain any detector that detects X-rays, including an image intensifier, a CMOS camera and/or a digital flat panel detector. In some configurations, the detector can have a substantially square shape with a length ranging from about 13 cm to about 15 cm. In other configurations, though, the x-ray detector 140 does not need to have a substantially square shape. In addition, the x-ray detector can have a pixel size that ranges from a square with dimension ranging from about 25 μm to about 200 μm, to a rectangle with the two dimensions of the rectangular pixel fitting in about the same range.

In some configurations, the X-ray detector can have a substantially square shape with a length of one side ranging from about 13 cm to about 15 cm. In other configurations, the X-ray detector can have a substantially rectangular shape with the shorter dimension ranging from 12 cm to 16 cm, and the longer dimension ranging from 18 cm to 24 cm. The X-ray source 135 can be contained in a housing that can be configured in two parts with a first part enclosing the x-ray source 135 and a second, separate part enclosing the x-ray detector 140. In other configurations, however, the housing can be configured so that it is a single part that encloses both the X-ray source 135 and the X-ray detector 140.

In some configurations, the housing 155 can also enclose a removable power source (such as a battery) and optionally an internal power supply. Thus, the power source and the power supply can be located internal to the housing 155 and also to the x-ray device 100. The supporting electronics for the power source and the power supply, as well as the supporting electronics for an image display and for wireless data upload, can also be located internal to the housing 155. Thus, in these configurations, the x-ray device 100 does not contain an external power cord or data cable. Incorporating the removable power source (i.e., the battery), the power supply, and the supporting electronics all within the housing allows the size and the weight of the device 100 to be reduced. With such a configuration, the power source can easily be replaced and delivers 60, 80, 100, 120, or even more x-ray images using just a single charge, with the exact number of images obtained with a single power source depending on the voltage and current parameters required for the images taken with a higher power setting reducing the number of images that can be obtained. Of course, if needed, the x-ray device 100 can be configured so that it is alternately, or additionally, charged using external power from a power cord that is plugged into a wall outlet. In other configurations, multiple power supplies can be provided for the source, detector, and control electronics, any (or all) of which can be located either internal or external to the housing 155.

In some instances, the X-ray device 100 contains a frame 150 that has an open configuration. As shown in FIGS. 1A and 1B, an open configuration gives a number of easy gripping options for a user to carry and hold the frame 150 during transport, and optionally during operation of the x-ray device 100. In some embodiments, the frame 150 can be configured as a modular unit so different cross members (or length members or handles) can be used to replace the existing cross members (or length members or handles). Thus, the frame 150 provides the ability for a user (or operator) to grip and hold the X-ray device 100 during operation, a feature that is useful since some other conventional C-arms can't be held in the hands while being operated because they do not have a suitable frame and because they are too heavy.

The x-ray device 100 can be activated by a trigger located anywhere on the x-ray device 100 that can be activated easily by the user. For example, the trigger could be activated near locations 151, 152, 153, and/or 170 on the C-arm. In other configurations, a separate foot switch that communicates with the x-ray device 100 using a wired or Bluetooth/wireless connection can be used. Indeed, the portable x-ray device 100 could be equipped with both a trigger on the device as well as a foot switch. The operation of any one of the triggers and/or the foot switch can also activate the image compression/decompression, handling, and video/image display functions both contained within the x-ray device 100 and on the separate image display device or tablet. In this manner, the surgeon, radiologist, medical practitioner, or other user can simultaneously control the manner in which the x-ray images are obtained by holding or guiding the x-ray device 100 while viewing the results obtained from the imaging on a conveniently-located display. This is one of the features enabled by the x-ray device 100. The ability to easily guide or manipulate the x-ray device 100 by hand while simultaneously viewing the image results enables the medical practitioner to obtain the x-ray images or video information needed to support the desired medical procedure in a manner similar to the way digital still and video cameras in cell phones and other personal electronic devices have enabled new and more effective ways to document, communicate, use, and share visual information. These configurations thus enable quicker and better medical decisions and encourage more frequent imaging "snapshots" during medical procedures which will lead to medical practitioners acting on better information, with the final result being better medical outcomes for the patient.

Figure 2:
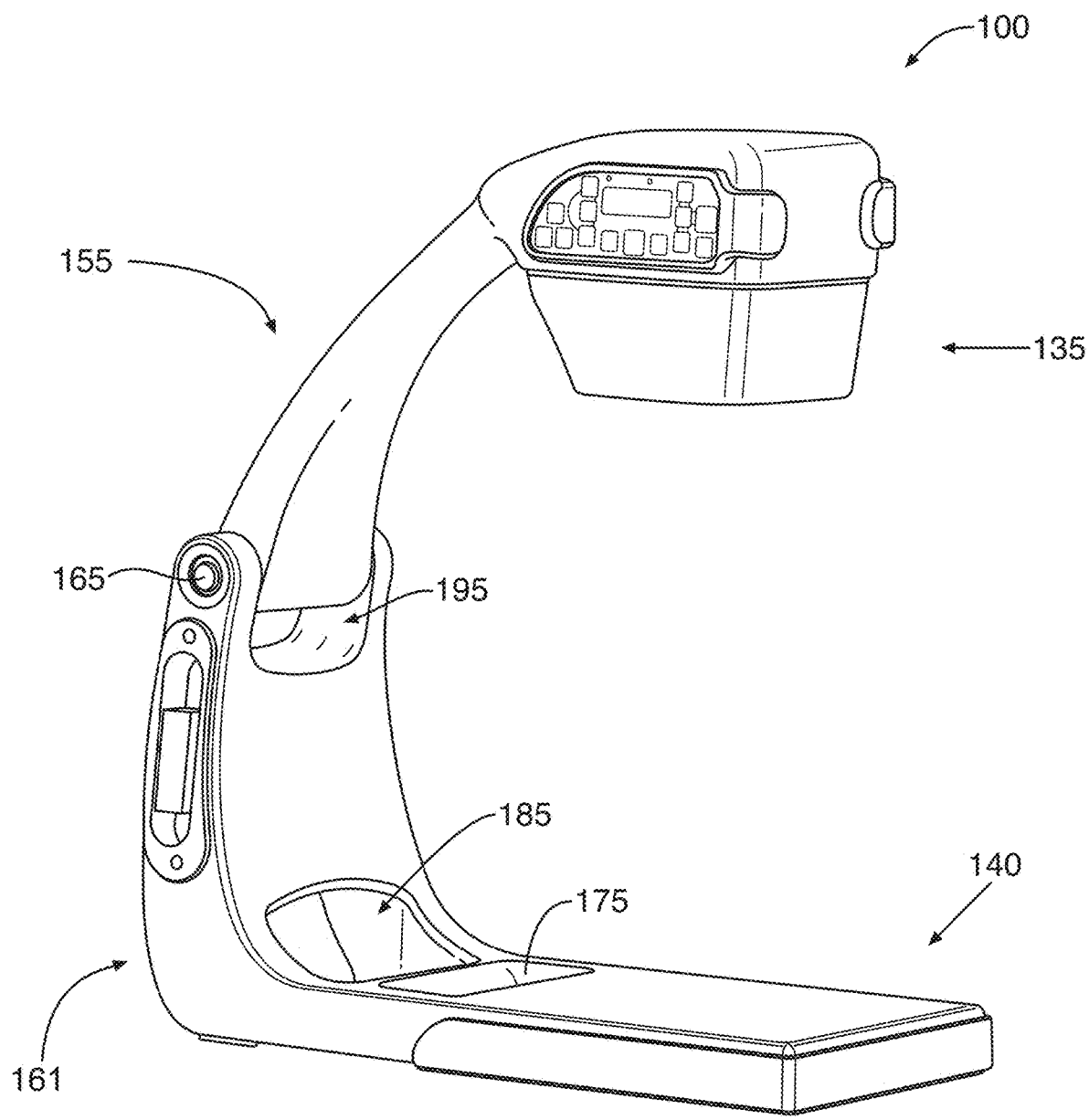
FIG. 2 shows another view of some embodiments of small, hand-held X-ray devices.

In other embodiments, the portable x-ray device 100 has the configuration illustrated in FIG. 2. In FIG. 2, the frame 150 has a first portion 156 that is part of the housing 155 that contains the x-ray source 135 and the associated electronics. The frame 150 also has a second portion 161 that is part of the housing 155 that also contains the x-ray detector 140 and the associated electronics. The first portion 156 of the housing and the second portion 161 of the housing are connected using hinge 165. The bottom of the portable x-ray device can contain an opening 175 and an opening 185 that can be used when attaching the x-ray device 100 to external support structure.

The portable x-ray device 100 has several features not exhibited by other C-arm devices. First, it has the capability of wireless data transfer, thereby eliminating the need for any wired connections or cables to the C-arm 105 or imaging arm. Second, it is internally powered by a removable battery or internal power source and, therefore, more portable than other C-arm devices which require a power cable. Third, it is lighter than other C-arm devices. As a comparison, the portable x-ray devices 100 described herein can have a weight ranging from about 10 to about 35 pounds while other C-arm devices have a weight ranging from about 40 to about 375 pounds. In other embodiments, the portable x-ray C-arm devices 100 described herein can have a weight ranging from about 12 to about 18 pounds.

Figure 3A:
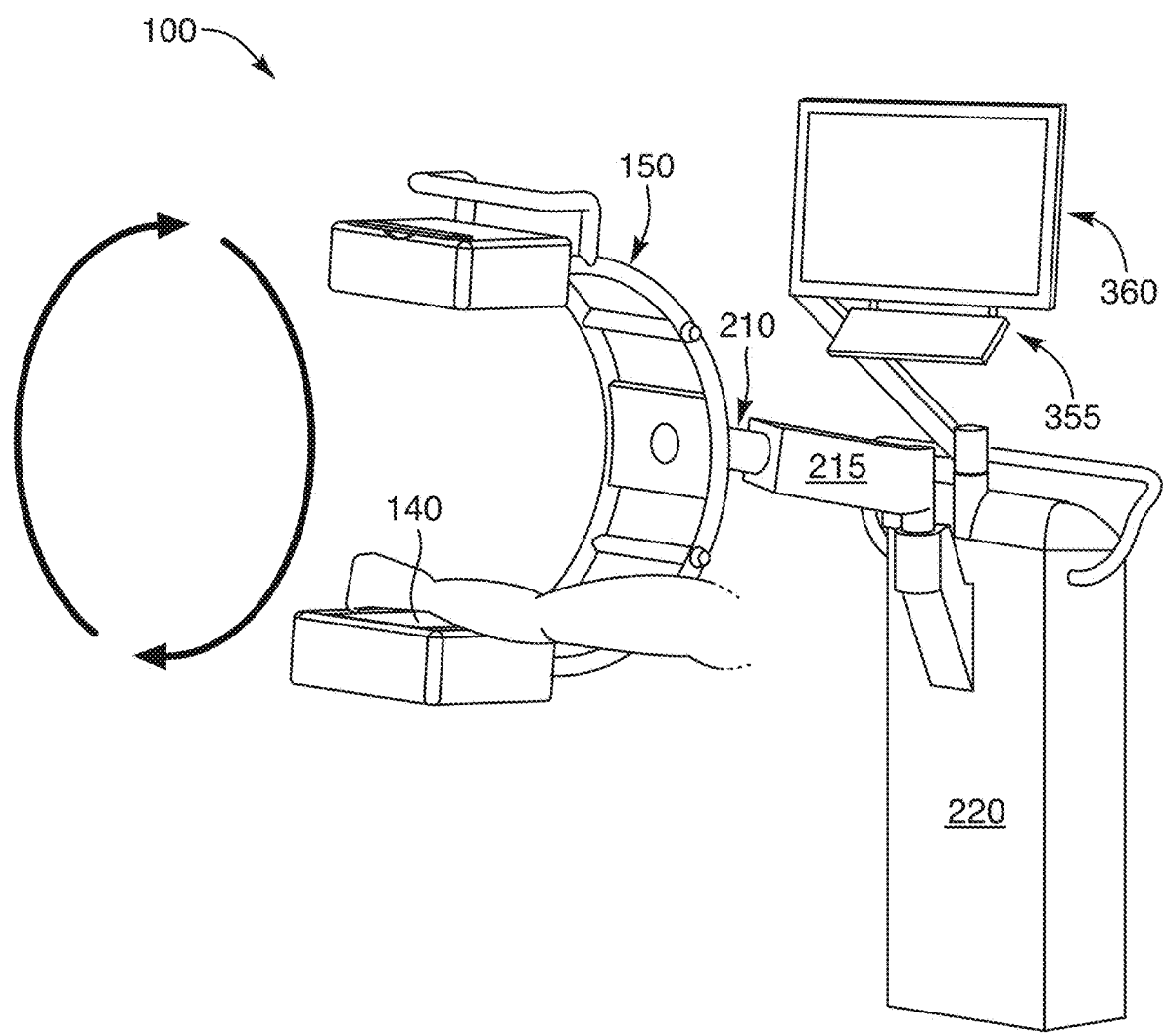
FIGS. 3A and 3B show some methods of using small, hand-held X-ray devices in an operating room.
Figure 3B:
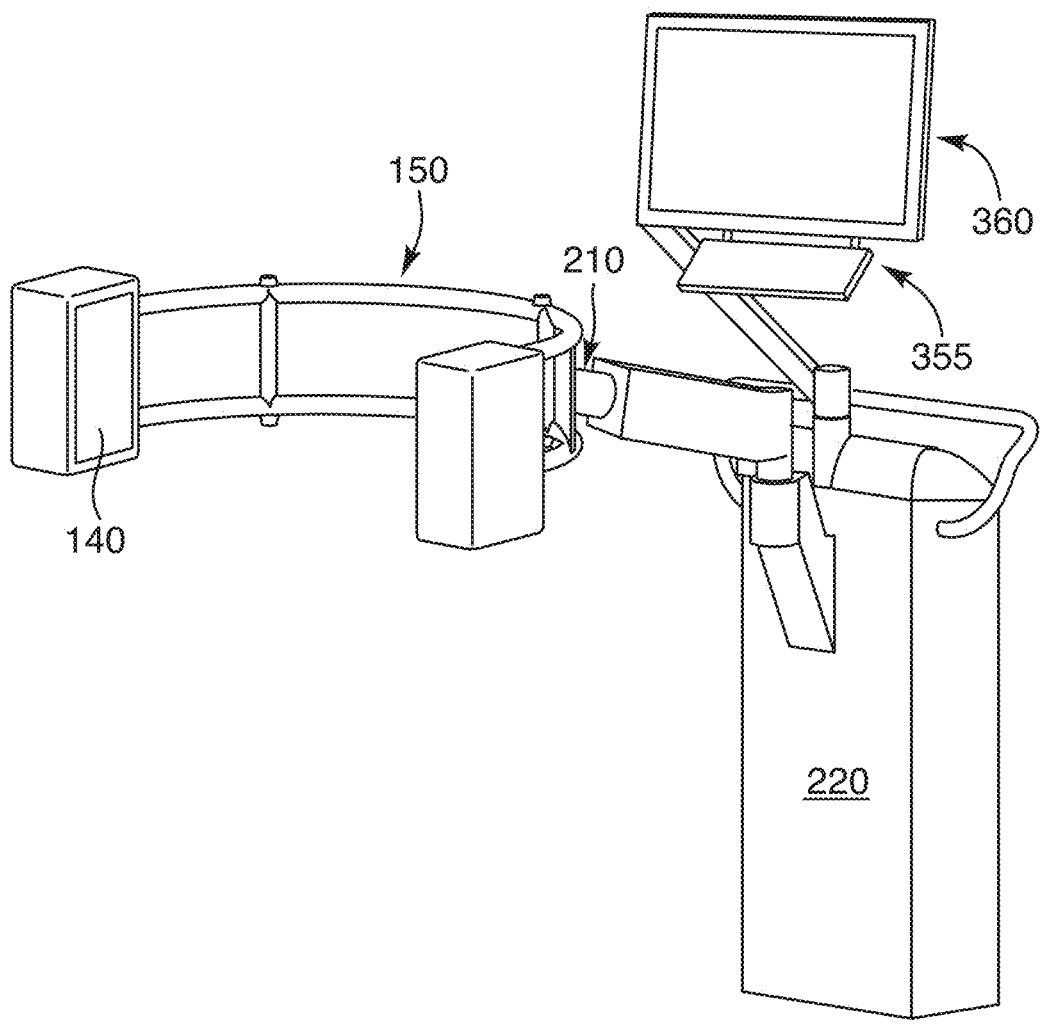
Figure 4A:
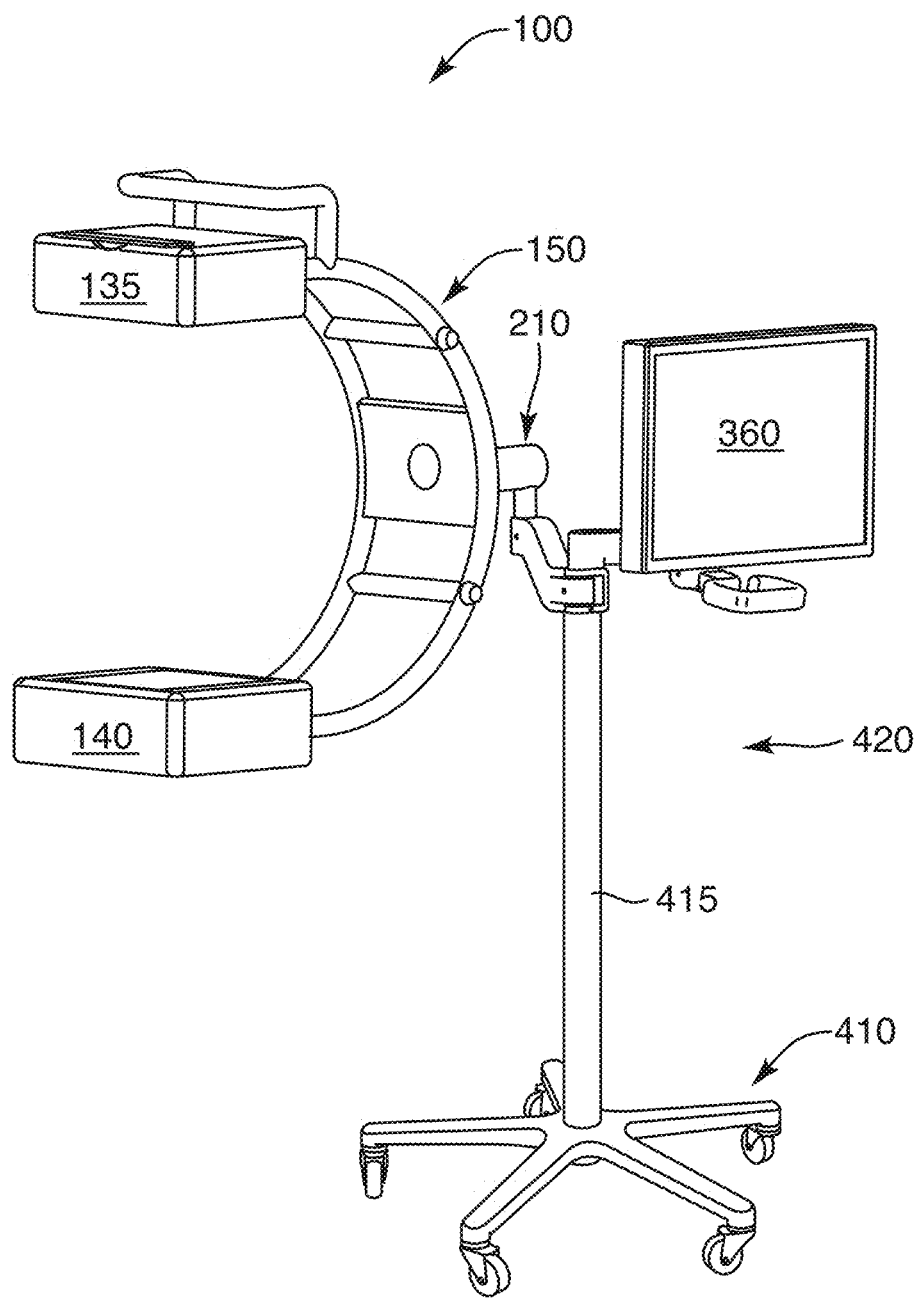
FIGS. 4A and 4B shows some embodiments of small, hand-held X-ray devices connected to a support structure.
Figure 4B:
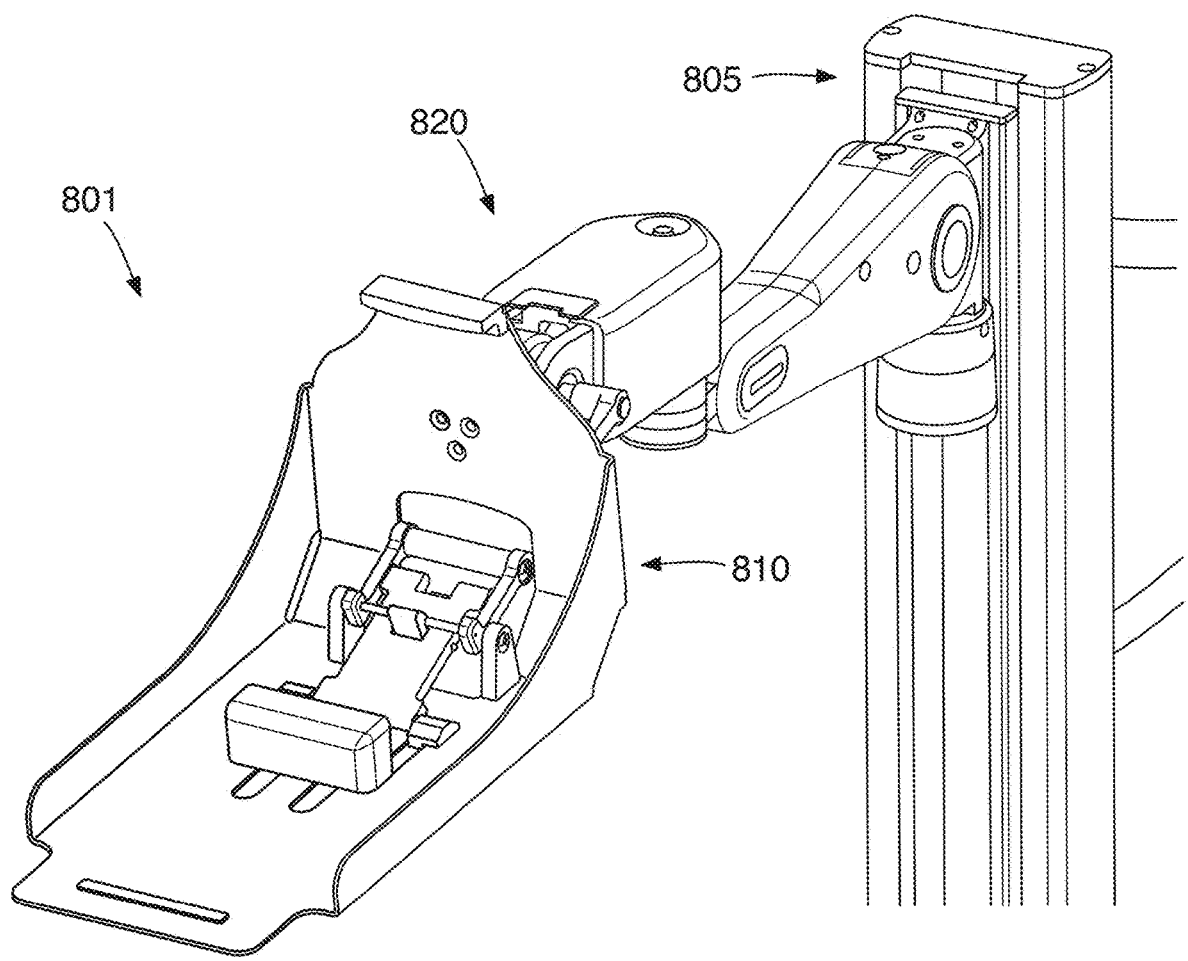

In some configurations, the portable x-ray device 100 can be connected to a stationary external (or support) structure so that it can rotate, or be positioned, around an object being analyzed, as shown in FIGS. 3A and 3B and as described in U.S. patent application Ser. No. 15/568,708, filed Nov. 23, 2017, the entire disclosure of which is incorporated herein by reference. This support structure contains a base 220, arm 215, tri-joint 210, input/output interface 355, and display device 360. In other embodiments, the portable x-ray device 100 can be connected to a mobile external (or support) structure for a similar purpose, as shown in FIG. 4 and as described in U.S. patent application Ser. No. 16/198,956, filed Nov. 23, 2018, the entire disclosure of which is incorporated herein by reference. Attaching the portable x-ray device to a support structure allows the operator to position the portable x-ray device 100 as needed for a series of imaging procedures, while freeing medical personnel to attend to other duties. As well, it leaves the hands of the operator free for other actions. For example, during a surgical procedure, attaching the portable x-ray device 100 to a support structure allows the medical person to take many actions, but then easily image the patient when needed using the pre-selected positioning of the portable x-ray device 100. When the surgical procedure is complete, the portable x-ray device 100 can be removed from the support structure and taken to another location for use or storage.

In other configurations, though, the portable x-ray device 100 can be connected to a movable support structure. In such configurations, the movable support structure can be configured to move across a floor while supporting the x-ray device 100. Thus, the movable support structure can comprise one or more wheels, shelves, handles, monitors, computers, stabilizing members, limbs, legs, struts, cables, and/or weights (to counterbalance the weight of the imaging arm and/or any other component and prevent tipping the movable support structure). FIG. 4 shows some embodiments in which the movable support structure 420 comprises a wheeled structure 410 connected to a stand 415 that contains a tri joint 210 that is connected to the x-ray device 100.

In some configurations, the X-ray device 100 and/or the external support structure can comprise any suitable locking mechanism that can selectively lock and unlock the rotation of the C-arm 105 around the object being analyzed. For instance, the locking mechanism can comprise a manually-engaged clamp, a detent mechanism, a motorized lock, an electric lock, a radio controlled lock, a remotely engaged clamp, and/or any other suitable mechanism that can be used to lock and release the orbital rotation of the c-arm. In some configurations, the locking mechanism can be part of the tri joint described herein or even an interface between the x-ray device 100 and the tri joint 210.

Figure 15A:
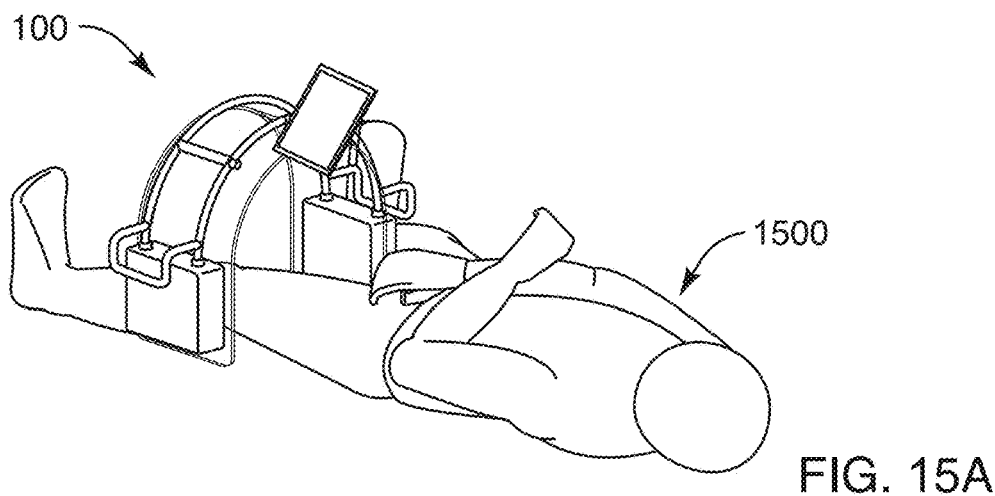
FIGS. 15A, 15B, and 15C show some embodiments of self-supported x-ray devices.
Figure 15B:
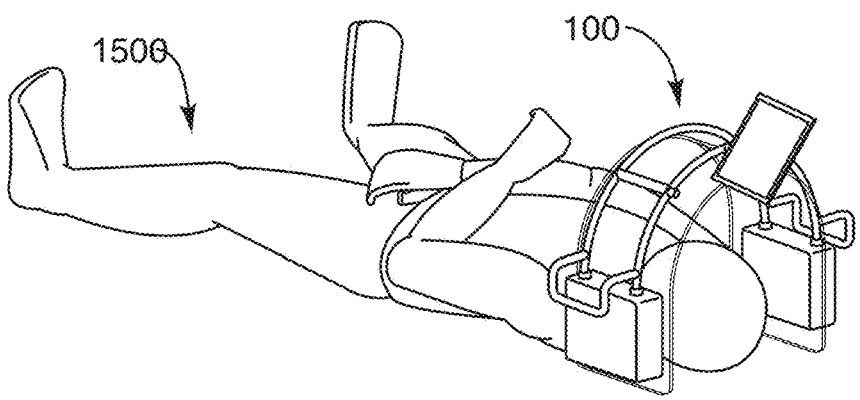
Figure 15C:
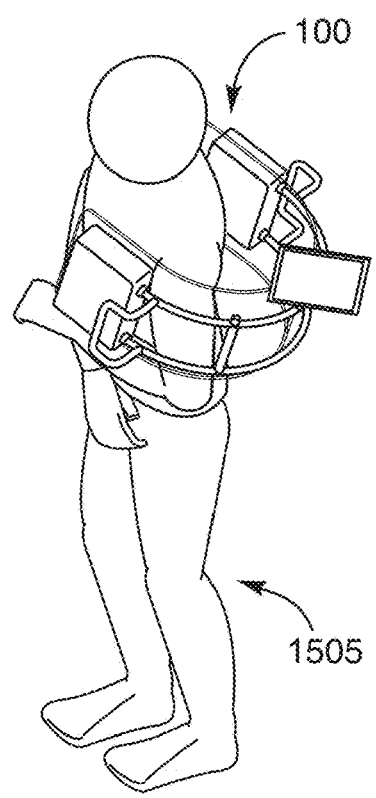
Figure 16:
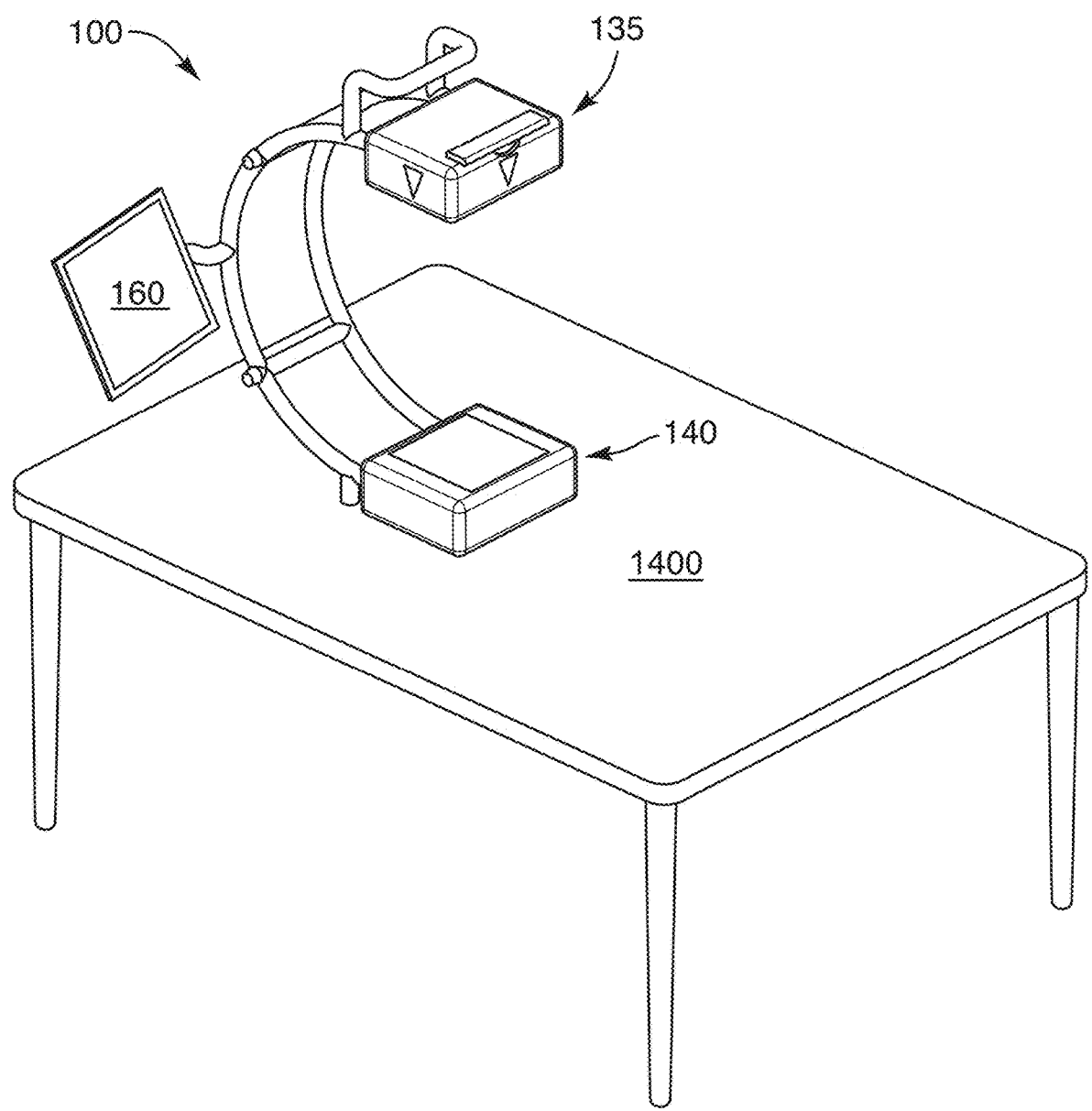
FIG. 16 shows other embodiments of self-supported x-ray devices that can be used with the sterile drapes.

In other embodiments, though, the X-ray devices or equipment need not be hand-held but instead can be self-supported. In these embodiments, the x-ray devices can be self-supported and still be used in a medical procedure without disrupting the sterile field near a patient. For example, the x-ray device 100 can physically be moved from one location to the next by hand as illustrated in FIGS. 15A, B, and C. The ability to move the x-ray device 100 from one location of a patient 1500 (i.e., the leg as shown in FIG. 15A) to another location (i.e., the head as shown in FIG. 15B), not to mention the ability to move the x-ray device 100 from one patient 1500 (i.e., patient in FIG. 15A or 15B) to another patient 1505 (i.e., patient shown in FIG. 15C), makes the x-ray device 100 extremely easy and convenient to use while supporting itself during any medical procedure. In other configurations, as shown in FIG. 16, the x-ray device 100 can merely rest on any surface, such as the top of table 1400, and then used during the desired medical procedure.

These hand-held (and self-supported) x-ray devices 100 can be used in or with surgical procedures and should therefore be made and maintained as sterile as possible. Thus, when used in sterile medical procedures, they can be at least partially or fully shrouded in a sterile barrier (or sterile drape) to protect the patient from contamination and/or infectious disease. Some conventional sterile barriers for C-arm x-ray devices consist of a sterile bag/sock that is placed over the x-ray source and another sterile bag/sock that is placed over the imaging detector. The exterior of the C-arm structure can be shrouded by a flexible barrier that may or may not connect to the bags/socks at the source and detector. However, in these conventional configurations, there is a break in the sterile barrier to provide access for the mechanical support structure and electrical cables to which the C-arm is connected. This break in the sterile barrier is a potential source for contaminating the sterile field.

Some conventional mobile X-ray imaging systems are typically draped with sterile drapes to cover both the X-ray source and the X-ray detector as well as some portion of the arm that supports the X-ray system. Sterile drapes are plastic sheet coverings that are placed over surgery tables, microscopes, and other devices used in the operating room during a surgical or medical procedure. In the particular case of a large x-ray imaging device, the typical draping procedure is to cover the x-ray source (which was typically over the patient) with such a drape and to place the detector under the patient and the table supporting the patient, where a drape was often not required. The purpose of this draping is to protect the patient since either the x-ray source or the detector may be over or near the patient, to protect the X-ray device from any body fluids or other fluids such as saline solutions that may be splashed, sprayed, or spilled in the vicinity of the patient, and to also protect the surgeon or other medical personnel because they may need to grasp various parts of the X-ray imaging system in order to adjust the position of the imaging system during the procedure and grasping the system through a sterile drape covering enables them to remain sterile while adjusting the position of the system. In draping these mobile systems, or the larger x-ray systems, the common practice has not been to close the sterile drape covering the system or the various portions of the system in a manner to form a sterile seal, but to simply leave the opening of the drape positioned far enough away from the sterile field surrounding the surgical area that there is no concern about a contaminant emerging from the opening in the sterile drape and contaminating the patient, the sterile drape, and/or the sterile field. This approach was workable because there was no way in which the sterile drape opening could be placed over or near the patient or the sterile field where the surgery was taking place.

Using the hand-held or self-supported x-ray imaging devices described herein, however, changes the concerns that must be addressed in applying a sterile drape. Since the surgeon or other medical personnel can touch any portion of the x-ray imaging device during its use, and any portion of the system (or even the entire system) can be positioned over, above, or near the patient during use, including the location where the opening of the sterile drape is located, the sterile drape design, and the way it is applied to the X-ray imaging system must be changed.

Figure 5:
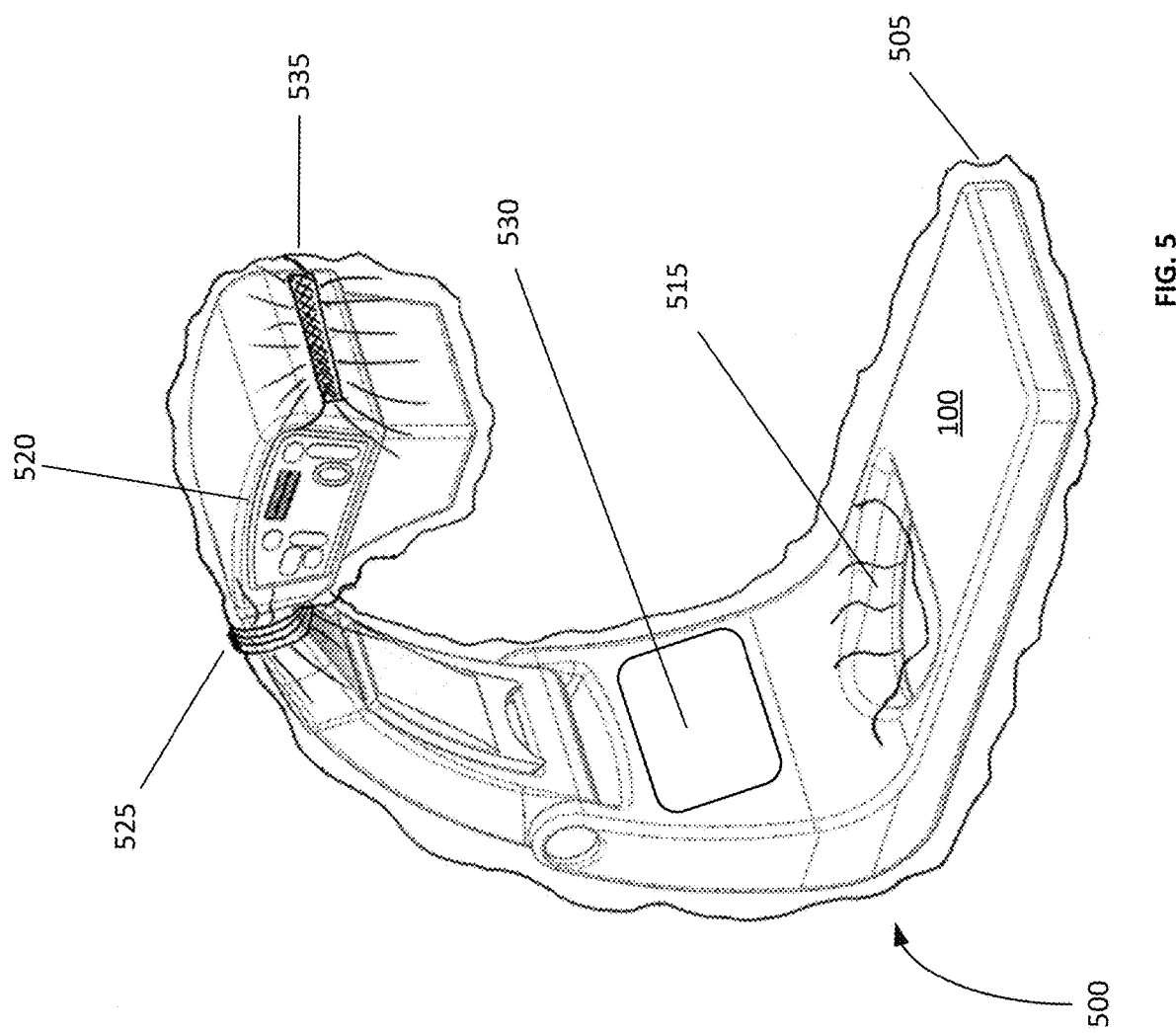
FIG. 5 shows some embodiments of a sterile barrier that can be used with hand-held x-ray devices.

In some configurations, the X-ray devices 100 contain a sterile drape or sterile barrier on the outer surface. The sterile drape can be closed or sealed around the x-ray device 100 in any manner that ensures that all the external surfaces are sterile and there is no opening left in the sterile drape whereby infectious agents or other contamination internal to the drape can emerge to contaminate a surgeon, other personnel in the operating room, or the patient. One example of these configurations is shown in FIG. 5 where the sterile drape 505 is applied over the X-ray device 100 so that the entire device 100 is contained within the sterile drape 505. The smaller size, and the portable and hand-held nature of the x-ray devices described herein allows the device to be substantially enclosed in a single, sterile barrier rather than using multiple parts or multiple sheets.

A number of features must be incorporated into the design of the sterile barrier to enable the sterile drape, and the x-ray device within the drape, to function while providing the necessary sterile field for the needed medical procedure. One of those features is that the sterile barrier can be made of a single sheet of a flexible material that is connected together at one end. This configuration allows the portable x-ray device to be enclosed in the single sheet and then the ends of the single sheet connected together. In other configurations, though, the sterile barrier is made of several sheets of material that are connected together to form a single sheet. And in other configurations, the sterile barrier can be made of multiple layers of a drape material that when combined, form a single sheet of the sterile barrier.

In some embodiments, the sterile barrier could be configured to be similar to a long stocking or a tube that is open at one end and closed at the other end. The tube or stocking is fed over one end of the C-arm x-ray device and pulled around to the other end of the C-arm and then the open end is closed. The open end can be located at any location of the x-ray device 100, including at the x-ray head (near the x-ray source), at the base by the detector, by the battery compartment, or otherwise along the back of the C-arm. The open end may also be closed using any method that temporarily closes the open end, thereby keeping the sterile field, while at the same time allowing the closure to be reversed so that the sterile drape can later be removed. In some methods, this open end can be closed by folding, rolling, and placing tape at the proper location so that it is wrapped around the C when properly folded. In other methods, the open end can be closed by using a sterile mechanical apparatus, such as a pin or a clip. In yet other methods, the open end can be closed by using self-adhering surfaces such as adhesive, hook and loop, or other self-adhering methods.

The open end (or hole) in the sterile barrier through which the C-arm is inserted can be covered by a sterile flap specifically designed into the barrier that is located at or near the opening. The sterile flap can be closed by use of adhesive means such as tape along with specific folding, rolling, or other means used to close the open end, including using a separate sterile covering. The flap may also include a self-adhering surface such as adhesive, hook and loop, or other self-adhering methods.

In some embodiments, the sterile barrier must be configured with a length so that the open end is far enough away from the surface of the x-ray device once it is inside of the sterile barrier. This configuration allows the closure process to begin some distance from the C-arm so that sterility is maintained throughout the closure process. Any excess air can then be forced out of the sterile barrier before the open end is closed. The excess material can then be folded or rolled back, using any techniques that maintain the sterility of the outer surfaces, towards the x-ray device so the contaminated interior surfaces are well enclosed within several folds or layers of sterile material, and the roll or bundle of folded material is then taped or otherwise secured to a suitable location on the x-ray device.

Some configurations of the installed sterile barrier 500 are depicted in FIG. 5. The sterile barrier 500 is configured to enclose substantially all of the x-ray device 100. The sterile barrier 500 comprises a sheet of any fabric or material that can remain sterile as long as needed. The sterile barrier contains an open end 510 in the sheet 505 through which the x-ray device is inserted and then the open end 510 is closed (or folded, or rolled) and secured with tape or a clip. To help the surface of the sterile barrier remain sterile, it can be folded at the open end where a user holds the material. So once the sterile barrier is placed in the desired position, the end can be folded so the sterile part of the fold remains in the sterile field while the unsterile part of the fold (previously held by the user) is located towards the x-ray device. The excess amount or length of the sterile barrier should be enough to accommodate this folded section, but without too much that would make it burdensome.

The sterile barrier 500 may be made of any flexible material that can be kept sterile under the conditions in which the C-arm device operates. In some embodiments, the material of the sterile barrier can comprise a plastic material such as polyethylene, a breathable fabric such as Tyvek, or a combination of both. In other embodiments, the material can be Mylar or polyethylene Terephthalate (PET) film, PVC film, HDPE and LDPE films, polypropylene, or any combination thereof. In yet other embodiments, any transparent breathable plastic material could be used that has a pore size small enough to contain bacterium (i.e., less than about one micrometer).

The sterile barrier 500 can be configured with several components that are useful for a user/operator of the x-ray device 100. A first component is a pocket, pouch, or pleat 515 that can be located in the area of the x-ray device 100 where a handgrip is located, as shown in FIGS. 5, 8-9, and 12-13. This pleat or pocket 515 creates additional slack or space within the sterile barrier allowing for a hand to be inserted in opening 175 (or opening 185), thus making it easier for the user to maintain a secure grip of the x-ray device 100 when it is enclosed in the sterile barrier 500, and without stretching or otherwise risking damage to or stress on the sterile drape material that may cause a tear or other damage that will negate the sterile barrier that is the purpose of the drape.

The pocket, pouch, or pleat 515 may contain an additional piece or section of drape material that is added to the drape at the appropriate location using "welding" or other attachment or joining techniques for joining two sections of drape material together that are known of the art. Alternatively, it may consist of some extra folds, gathers, or tucks of material that are made at the appropriate location in the drape material as it is manufactured. Again, a small spot or portion of the gathers or tucks may be welded, glued, or otherwise fastened into place to preserve an extra amount of the drape material at the appropriate location even if the sterile drape is pulled and stretched during the process of installation over the x-ray imaging device 100.

A second useful component of the sterile barrier 500 is a flexible, transparent portion 520 that is located over the control interface of the x-ray device 100, making it easy for the user to view and manipulate the controls of the x-ray device even though the sterile barrier 500 is present. This flexible, transparent portion 520 can be configured similar to the size of the control interface. Of course, additional flexible, transparent portions could be incorporated into the sterile barrier wherever it is needed to view control panels or other similar structures on the device 100.

A third useful component of the sterile barrier 500 comprises a strap 525 that can be used to partially or completely wrap around a portion of the x-ray device 100 (and a portion of the sterile barrier 500) and used to aid in gripping/holding the x-ray device 100. The strap 525 gathers the material of the sterile drape together around any desired location (i.e., a handle) so that the x-ray device 100 may be easily grasped for transport or operation without first having to gather excess material, move it out of the way, or otherwise contend with the excess drape material at the handgrip location which can be necessitated in some configurations by the need to pass the larger portions of the C-arm through the sterile drape as it is installed.

A fourth useful component of the sterile barrier comprises making a portion of the sterile barrier act as a vent 530. This vent can be made with an air-filtering and/or breathable material that allows excess air within the sterile drape to exit the sterile barrier while preventing any contamination from exiting the sterile barrier, thereby reducing any excess air pressure in the sterile barrier 500 once it is sealed together. The vent 530 of the sterile barrier can be made using any breathable microbial fabric or other microbial filtering material that can be incorporated into the sterile barrier. The vent 530 helps avoid the sterile barrier from ballooning and/or containing too much air. So in some embodiments, the vent 530 can be made with any mechanism that allows the air within the sterile barrier to exit through the vent but not enter.

Figure 14:
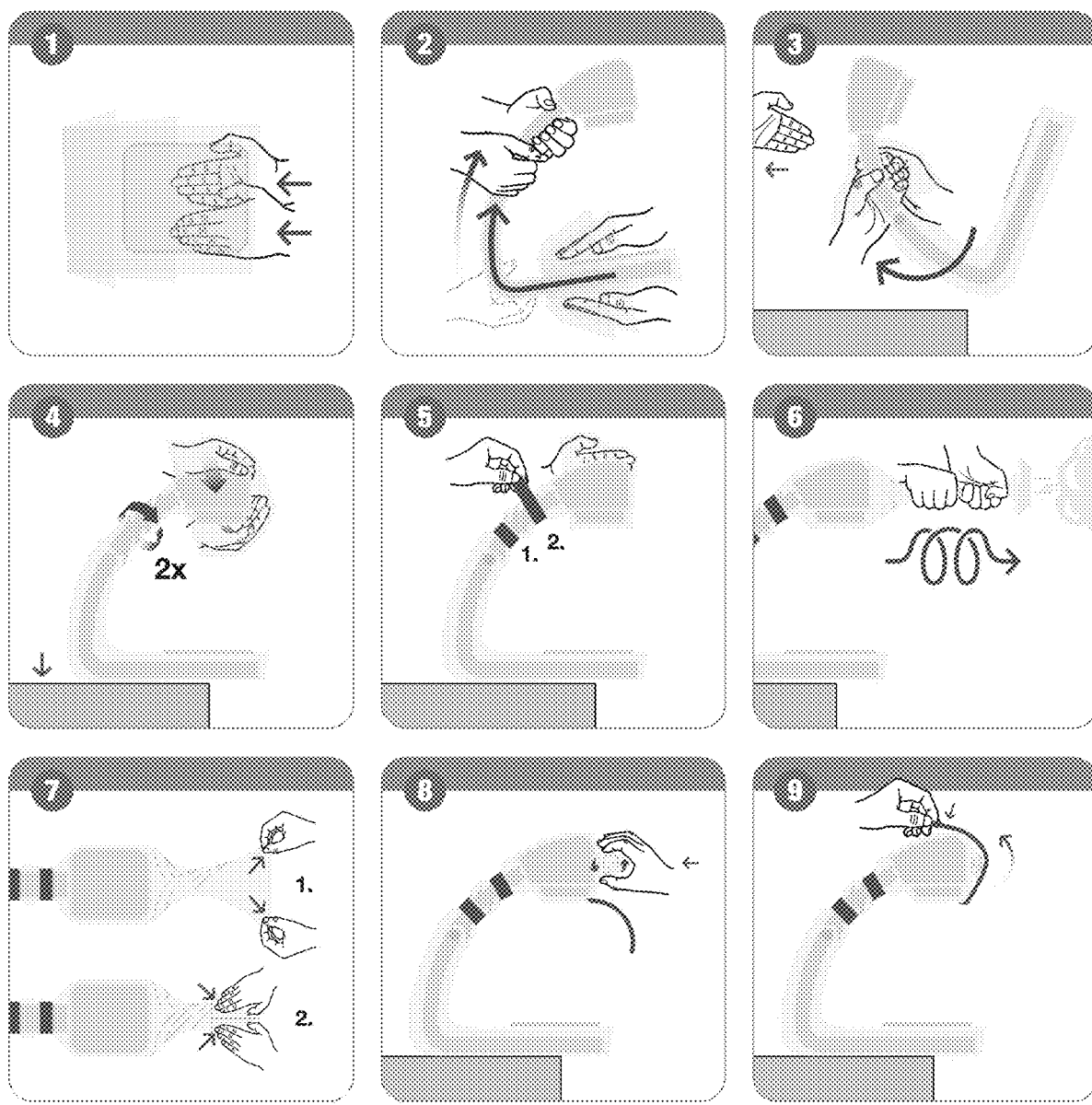
FIG. 14 shows some embodiments of methods for installing a sterile barrier on hand-held x-ray devices.

In other configurations, alternative methods can be used to resolve the problem with excess air enclosed within the sterile drape. In these configurations, the sterile drape can be installed in a manner that will force the excess air out of the opening in the sterile drape during the installation process. One method for accomplishing this air removal can be to rotate, twist, or wind the material of the sterile drape around the x-ray device structure at various suitable locations while it is installed. This method can also be accomplished by rotating or twisting the material of the sterile barrier as it is being installed on the x-ray device to constrict the drape around the frame of the device, as shown in panel 4 of FIG. 14. This action not only forces excess air out of the sterile barrier, but also helps the sterile barrier conform to the outer surface of the x-ray device, making the combination of the sterile barrier less bulky and reducing the amount of air flow in and out of the sterile barrier. One example of this method is shown in FIG. 14.

Figure 6:
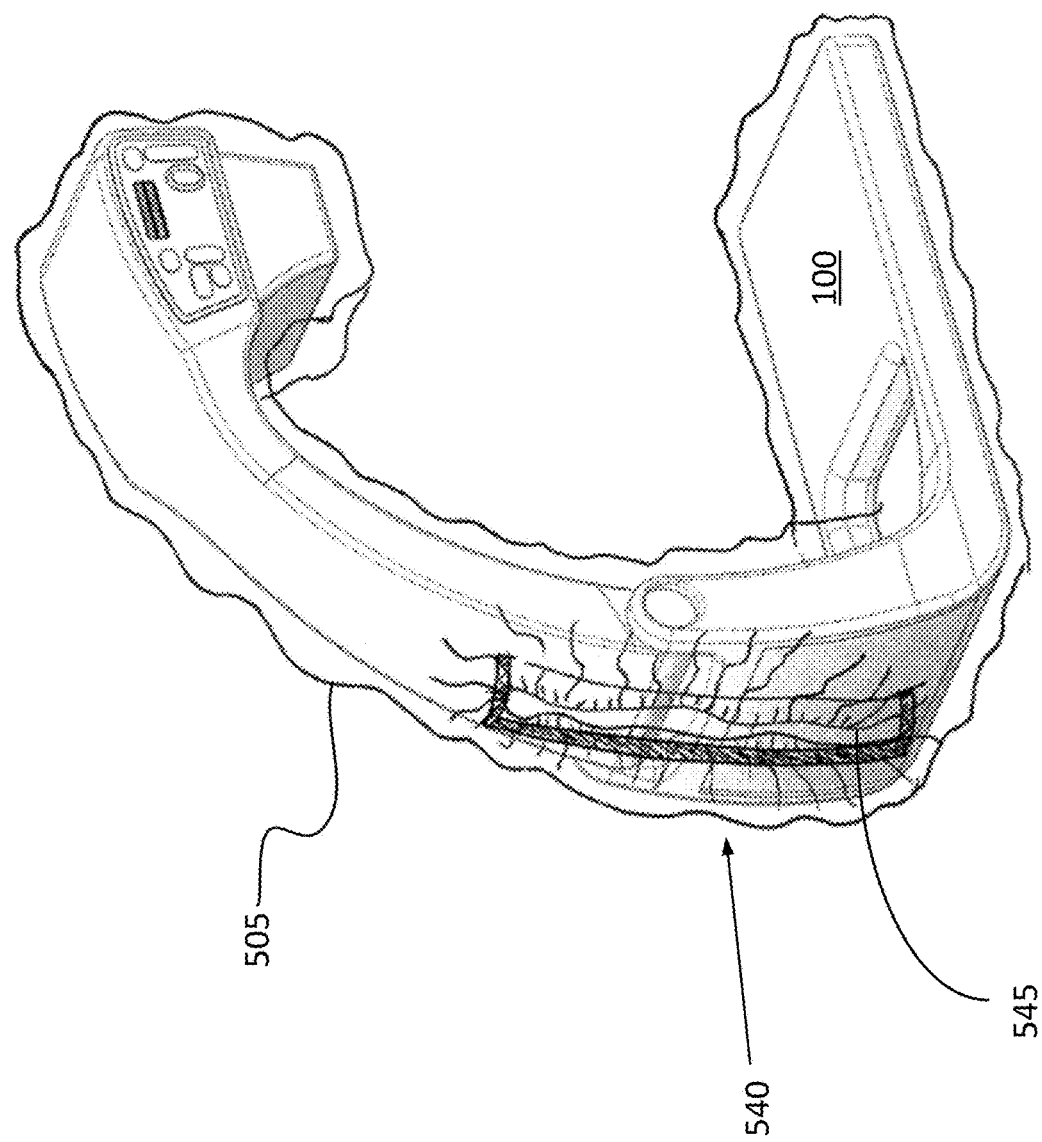
FIGS. 6-7 show other embodiments of the sterile barrier that can be used with hand-held x-ray devices.
Figure 7:
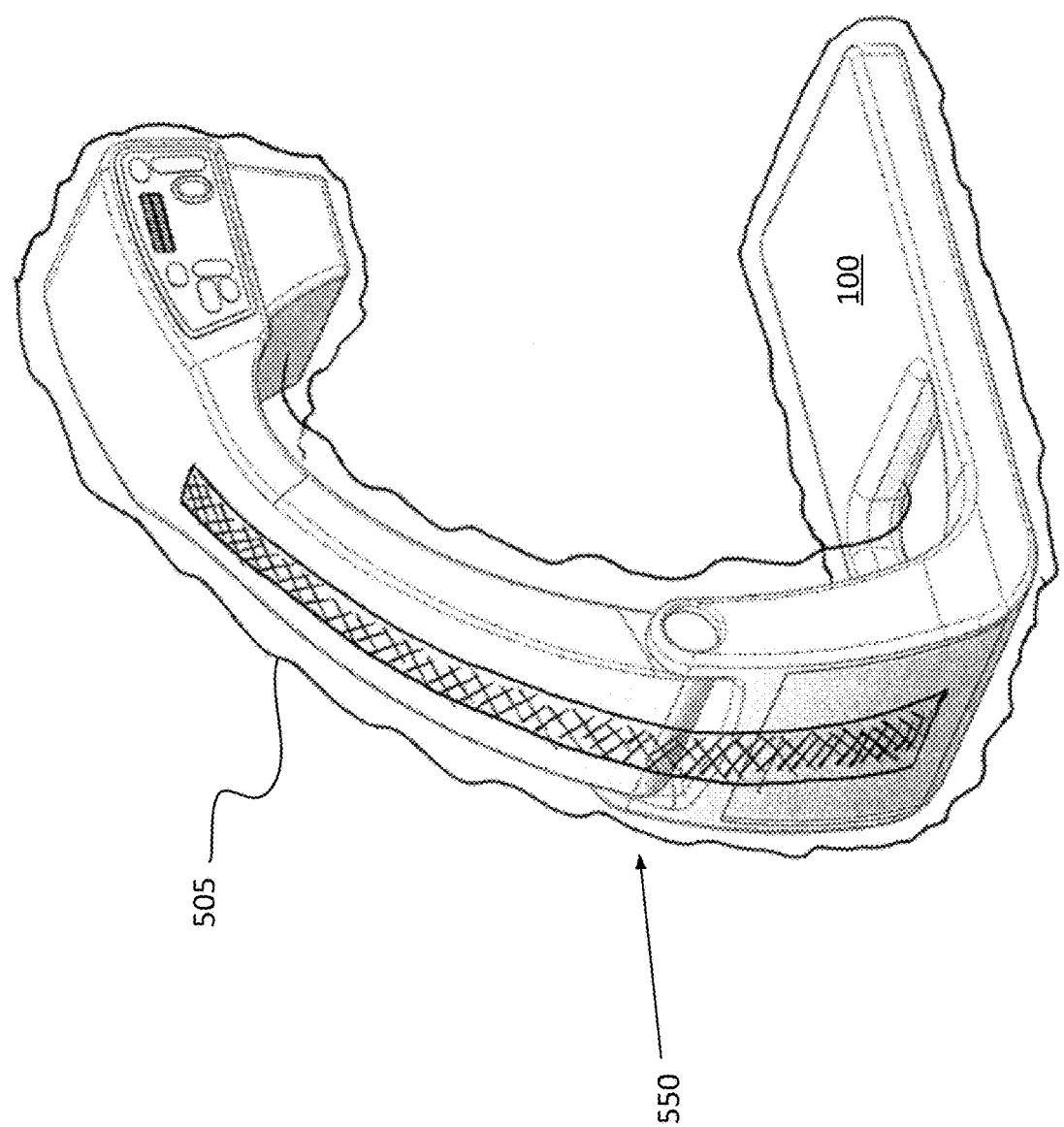

Other configurations of the sterile barrier or sterile drape are illustrated in FIGS. 6-7. In FIG. 6, the sterile barrier 500 can be configured with a small opening 540 through which the x-ray device 100 is inserted to install the sterile drape on the device. The small opening 540 includes a flap 545 that is used to close the small opening 540 using a self-adhesive means. FIG. 7 shows a similar configuration where a larger opening 550 is used and can be closed in a similar manner.

Figure 10:
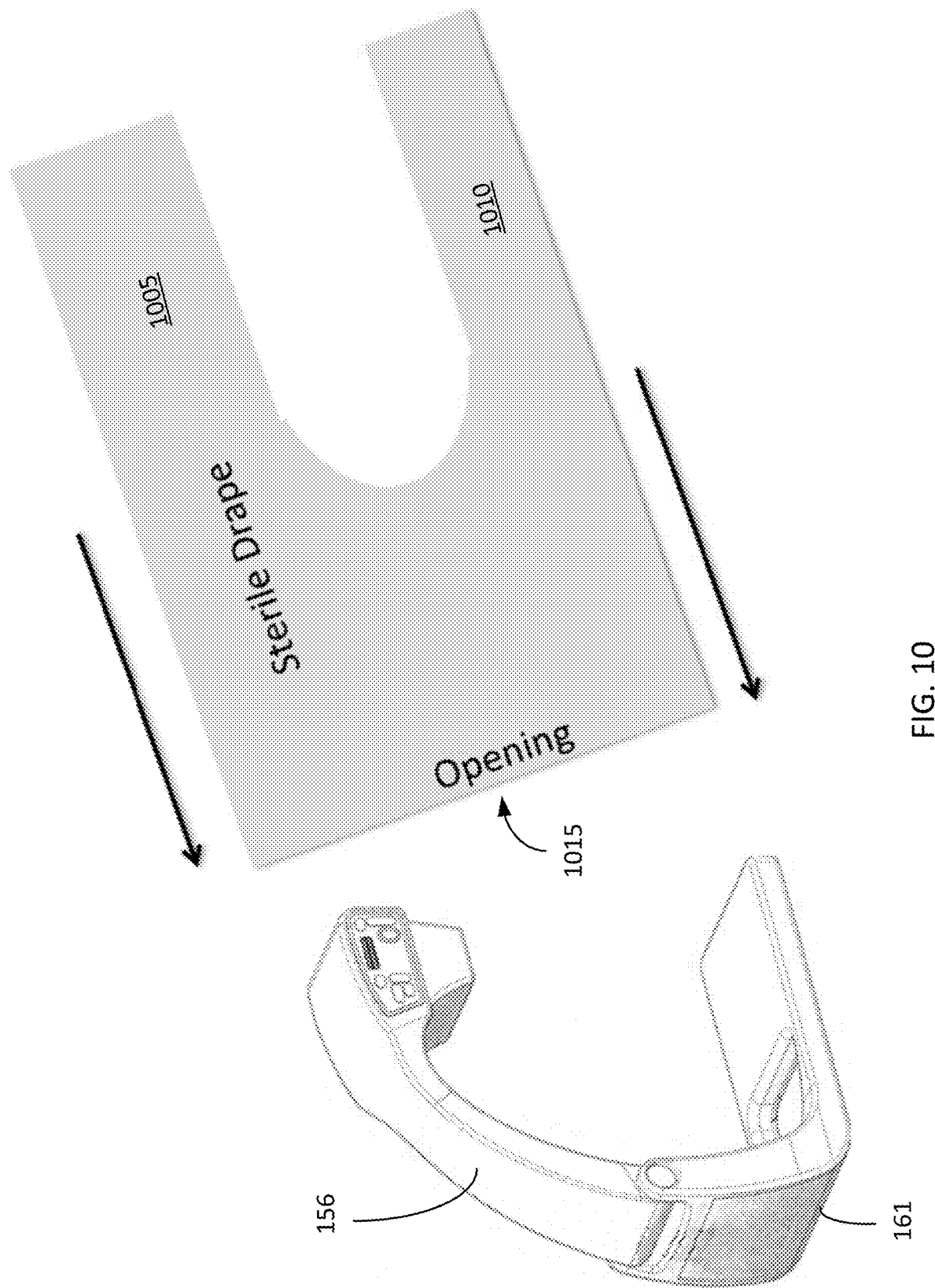
FIG. 10 depicts some embodiments of the sterile barrier.

In similar configurations, the sterile barrier can be configured similar to a 2-fingered glove 1000 or a pair of pants, as shown in FIG. 10. The first part 156 of the x-ray device 100 and the second part of the x-ray device 161 are inserted into the two fingers (1005, 1010) of the glove 1000. The opening 1015 of the glove can then be closed along the back of the C-arm device, again using any technique to maintain the sterility of the outer surfaces.

The sterile barrier 500 needs to retain its structural integrity while the x-ray device is being operated. If the sterile barrier 500 is punctured, torn, or otherwise damaged to create a hole or opening, or if the seal or closure applied to close the sterile drape opening by which the drape is applied over the x-ray system fails, then the sterile field for the x-ray device 100 and/or the surgical field may be contaminated. Therefore, the sterile drape must have design features and characteristics that prevent and/or substantially reduce the likelihood that the closure of the sterile drape fails, or that the drape be punctured, torn, or damaged during use.

The sterile drape can be damaged by stretching, tearing, or a puncture that could be caused by a medical instrument, or by the fingers of a hand that is holding or manipulating the x-ray device when contained within the drape. As shown in FIG. 5, there are several features provided within the x-ray device 100 that might damage the sterile drape because these features represent points at which the user of the x-ray device must grip, hold, or otherwise interact physically with the X-ray device. These features include handgrips or handles, the buttons or other control surfaces, and the corners, edges, and contours of the x-ray device where the user may grip or hold the device, as well as where the drape may be stressed when the device is placed on a table or other supporting surface or structure.

Figure 11:
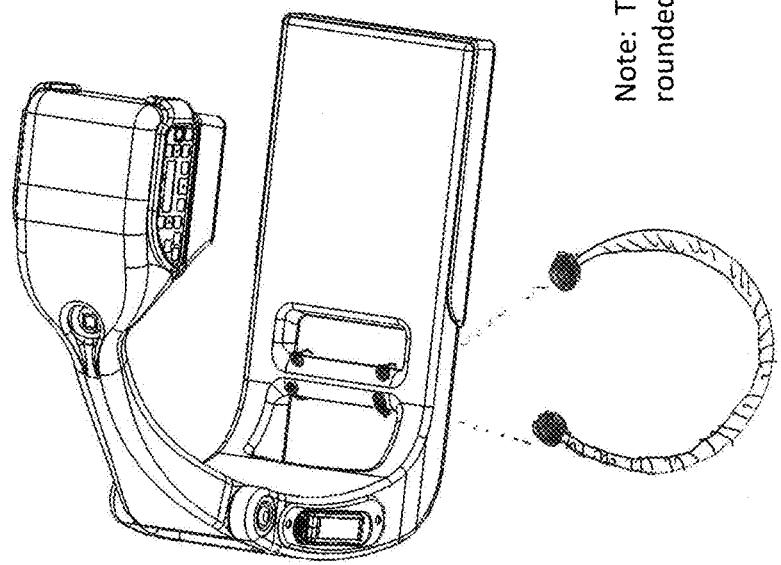
FIG. 11 depicts some embodiments of the clips that can be used with the sterile barrier.

There are several techniques that may be employed in the design and fabrication of the sterile drape to deal with these damage concerns. The first technique would be to provide some looseness or room in the over-all size and configuration of the sterile drape. A second technique that may be used is to ensure that there is sufficient slack or looseness in the sterile drape at key locations so that the sterile drape is not stretched or stressed when it is picked up, held, or otherwise manipulated by the handles or grips. A third technique would be to use one or more clips 605, as shown in FIG. 11, which may be used when the drape is applied to the x-ray device 100. The purpose of these clips 605 is to ensure that sufficient space, slack, or looseness in the draping material is gathered at the appropriate location, such as at the location of any handle or grip so that when the user needs to grasp or grip the handle, there is room or looseness within the drape to accommodate the user's fingers wrapping around the handle to ensure a secure grip.

The clips 605 can be applied or used as part of the procedure by which the sterile drape is placed over the x-ray device 100. Once the sterile drape has initially been placed on the device, the clips would be placed around any handle or grip, typically with one clip on each end of the handle or grip. While the clip is being placed, the installer may tuck or move extra drape material into the area around any handle to create a cavity or space within the drape so that the clip can be applied to the handle without stretching or stressing the drape material. Once positioned, the clip will maintain the cavity or space so that a hand may be able to easily grasp the handle at any time without having to pause to re-position the drape material or to re-create or to enlarge the cavity that was initially formed when the drape was applied.

Figure 8:
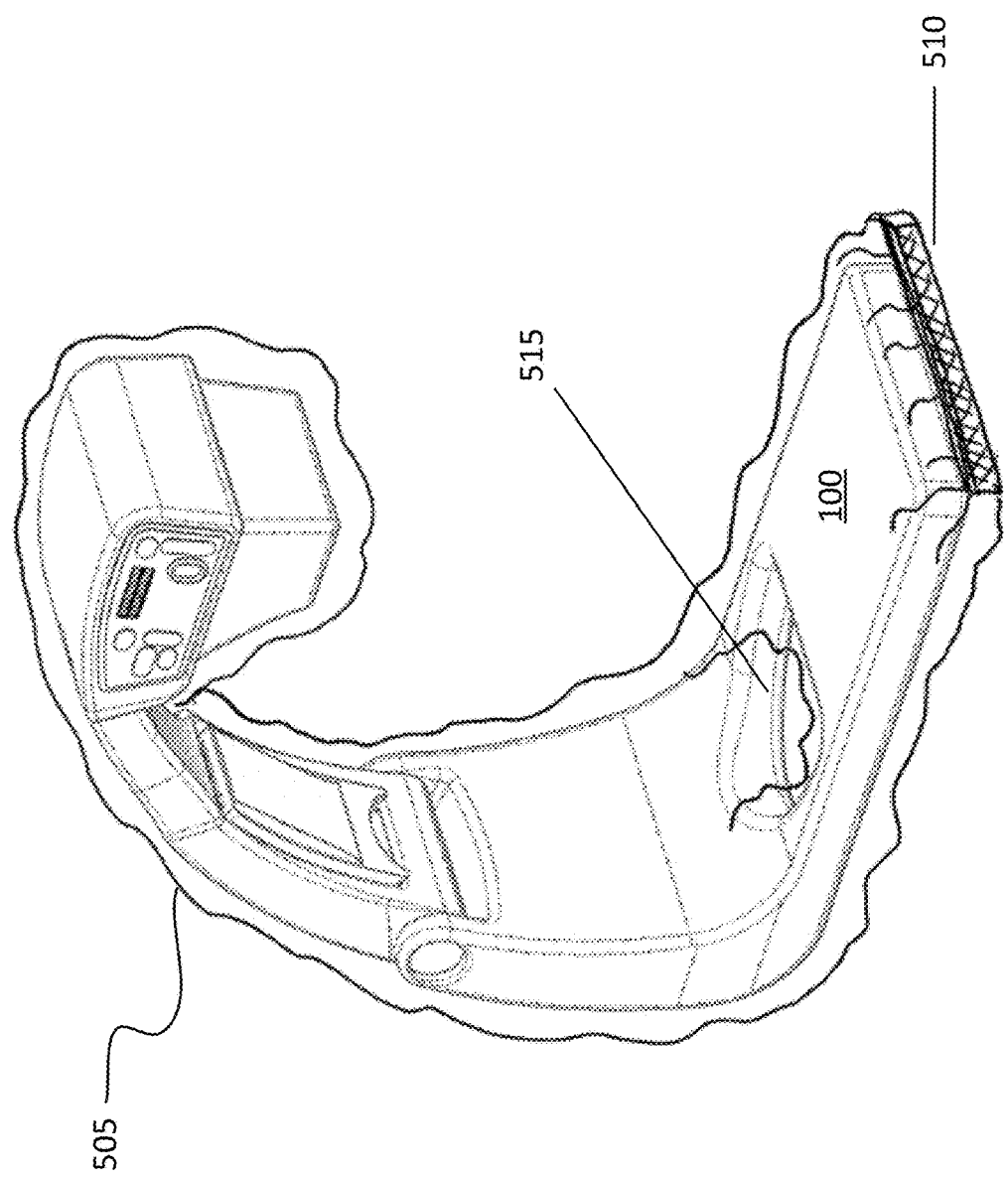
FIGS. 8-9 show yet other embodiments of the sterile barrier that can be used with hand-held x-ray devices.
Figure 9:
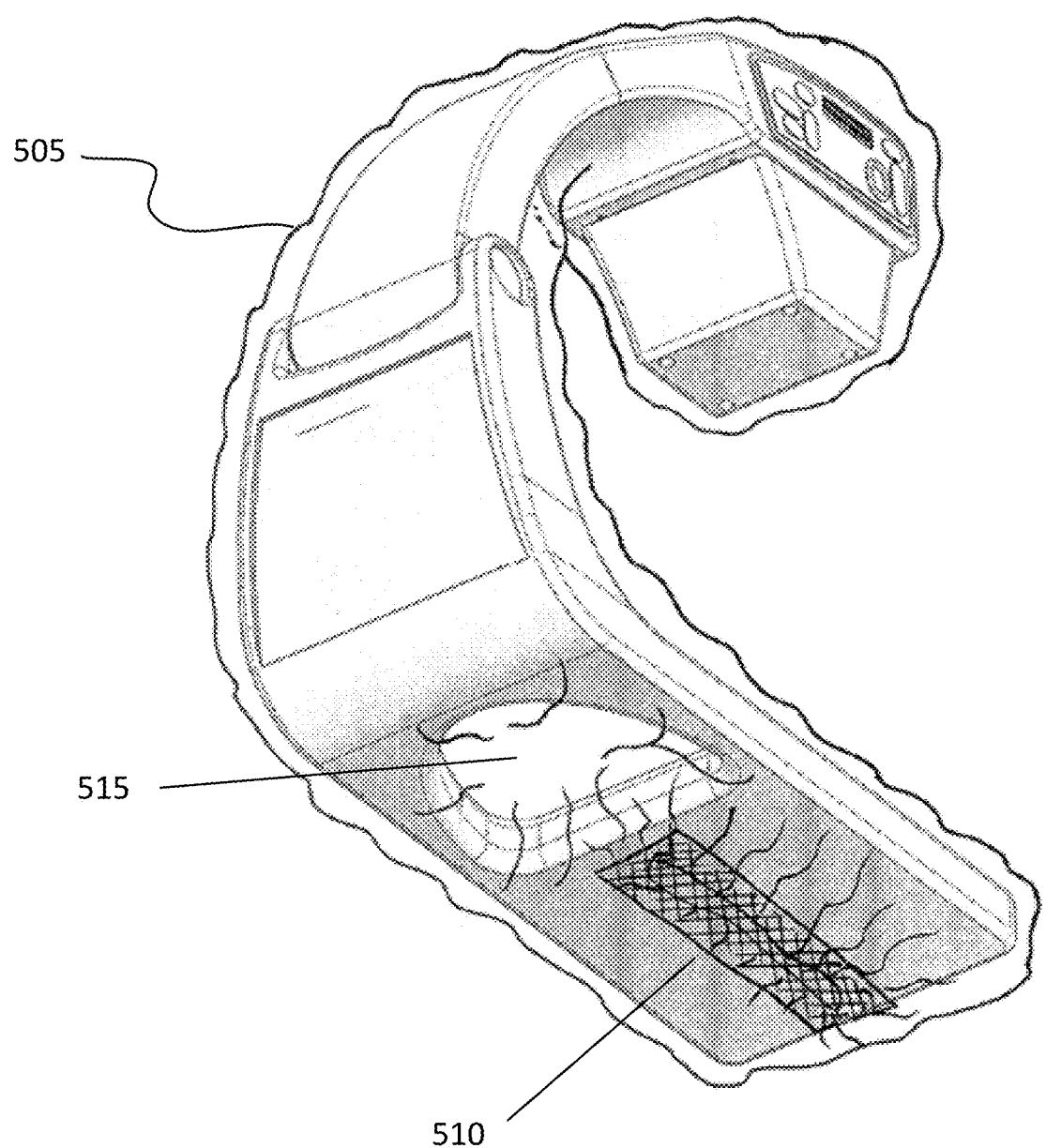
Figure 12:
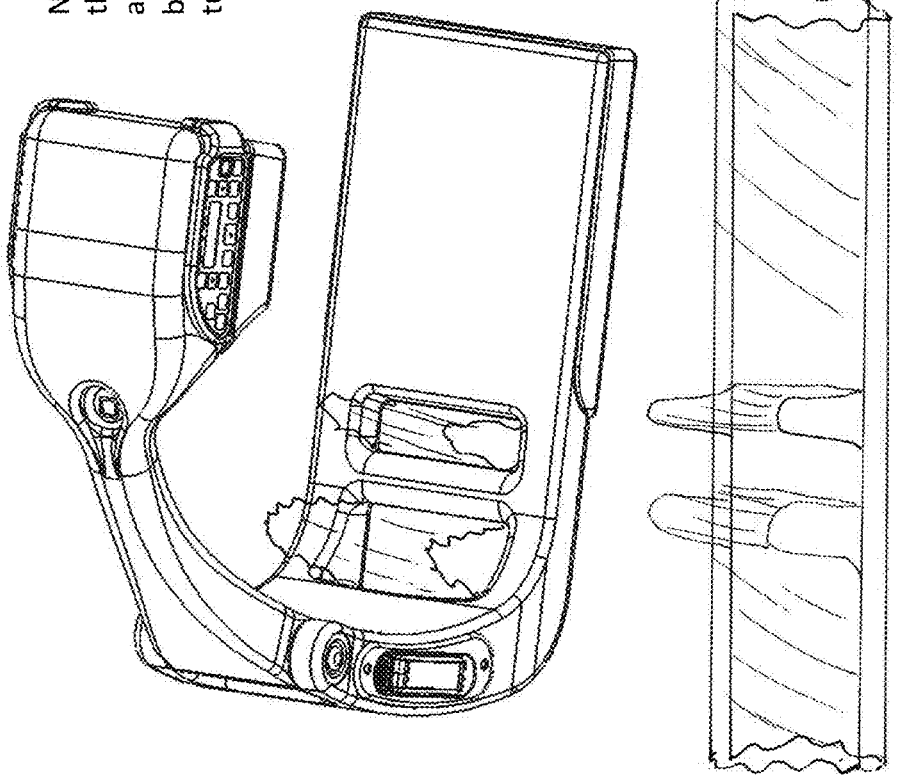
FIGS. 12-13 depict some embodiments of the pockets that can be used with the sterile barrier.
Figure 13:
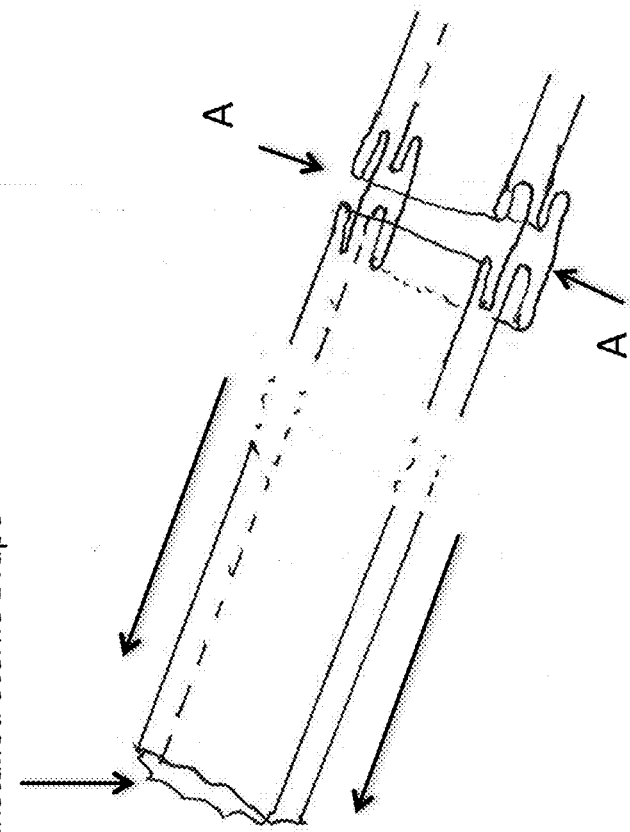
Figure 13:
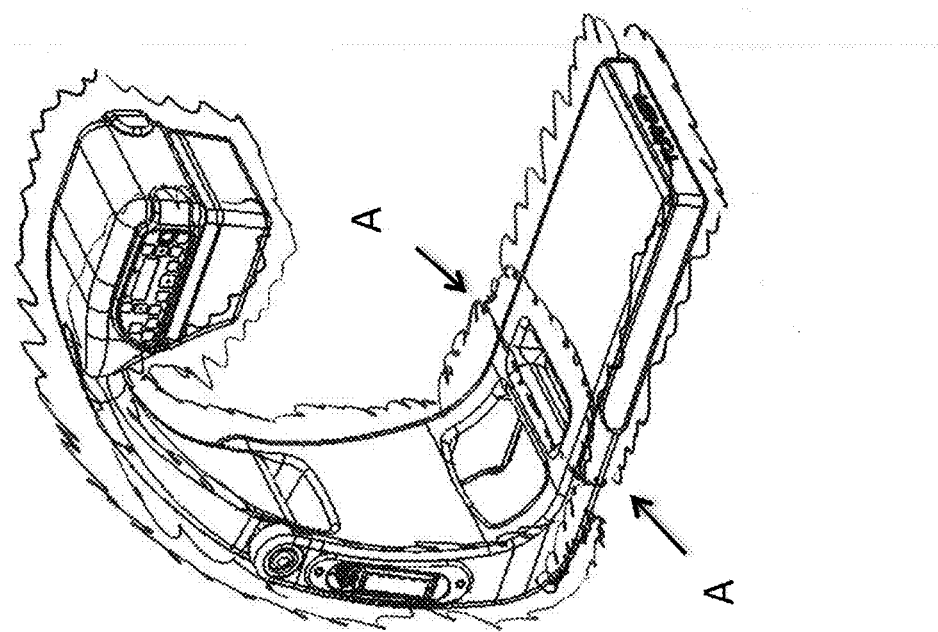

In addition to, or instead of the clips 605, the sterile drape may be formed with one or more pouches or pleats in the material at the time of manufacture, as shown in FIGS. 8-9 and 12. These pouches or pleats 515 would be positioned within the body of the sterile drape so that when it is fully and properly applied to the x-ray device, the pleats or pouches are located adjacent to the handles or grips where extra slack, space, looseness, or room is needed in the drape to accommodate a hand while gripping the handle. If properly designed, these pleats or pouches are stable in their position on the x-ray device, and in their function to provide room for a hand-hold, or they may be accompanied by the use of clips 605 to ensure that the cavity for the hand grip is always available.

In some embodiments, the x-ray devices can be mounted to a separate support structure as shown in FIGS. 3A, 3B, 4A and 4B. As shown in the embodiments depicted in FIG. 4B, a clamping device 801 contains a cradle 810 so that it mates with the surface of a portion of the x-ray device 100. Cradle 810 contains a connecting member 820 that is used to connect the clamping device 801 to an external support structure 805. The connecting member 820 counterbalances the roll, pitch, and yaw motions of the x-ray device 100. In these embodiments, the cradle 810 has features, protrusions, or mounting guides that help ensure the x-ray device 100 is securely attached to the support structure, while also ensuring that it is easy to remove the x-ray device from the support structure again if desired. Again, the sterile drape will need to be designed to accommodate such features. This can be done in a similar manner to that described for a handle, by designing a pouch or pleat into the body of the drape at the appropriate location so that when the drape is properly applied to the x-ray device, the necessary slack, looseness, or space is available at the proper location on the body of the x-ray device. Again, one or more clips may be used to help secure or maintain this cavity, or the user may simply use their fingers to manipulate the pleat or pouch to ensure it is properly located when the x-ray device is mounted to the separate support.

In some embodiments, the sterile barrier can be configured to cooperate with a sterile barrier located on the surface on which the C-arm is placed. So when the sterile barrier is placed on a surgical table, the cradle, or any other surface, the sterile barrier located on the C-arm can be connected with a sterile barrier that is located on that surface. For example, one end of the sterile barrier could be configured to mate with a separate sterile barrier that surrounds the surgical table or cradle.

In other embodiments, the sterile barrier on the C-arm can be configured so that it can expand to cover a portion of the surface on which it is placed. In these embodiments, the sterile barrier can be configured with an additional portion(s) that covers the surface of the object on which they rest. For example, the sterile barrier could be configured with an extra length of material that also enclosed the cradle in which the C-arm rests.

Using the sterile barrier, the C-arm x-ray device 100 can be handled by a sterile operator and positioned in any sterile field without compromising the sterility of the field or the operator. Indeed, having the C-arm x-ray device 100 fully enclosed in a sterile barrier prevents contamination of a sterile operator or the sterile field.

It is desirable in many applications that a protective shield or additional barrier be incorporated into the sterile drape. A common example is what is commonly called a k-wire plate or shield. A k-wire is a wire that is often used in hand surgery to repair or strengthen broken bones in the hand by inserting the wire into a bone using various techniques. These wires are often inserted under x-ray observation in order to obtain the desired placement in the patient's hand. This procedure requires that the hand be placed on or immediately next to the x-ray detector. Since the procedure is performed essentially on the sterile barrier, the k-wire may inadvertently puncture the sterile barrier as it is manipulated by the surgeon, so a shield is placed to guard against this type of common error that would render the sterile covering or barrier ineffective. These protective plates can be added on top of the sterile barrier, or they can be included as part of the sterile barrier when it is manufactured.

Because of the hand-held nature of the x-ray device 100, the sterile barrier can be hypothetically installed by a single operator. In this installation, the x-ray device 100 can be rested on a table, cradle, stand, or support structure. The sterile barrier can be installed using one hand while the other hand of the operator is used to manipulate the x-ray device. As well, the sterile barrier can be installed by two people when a table, stand, or supporting structure is not available, with one person holding/manipulating the x-ray device and the other person manipulating the sterile barrier.

Figure 17:
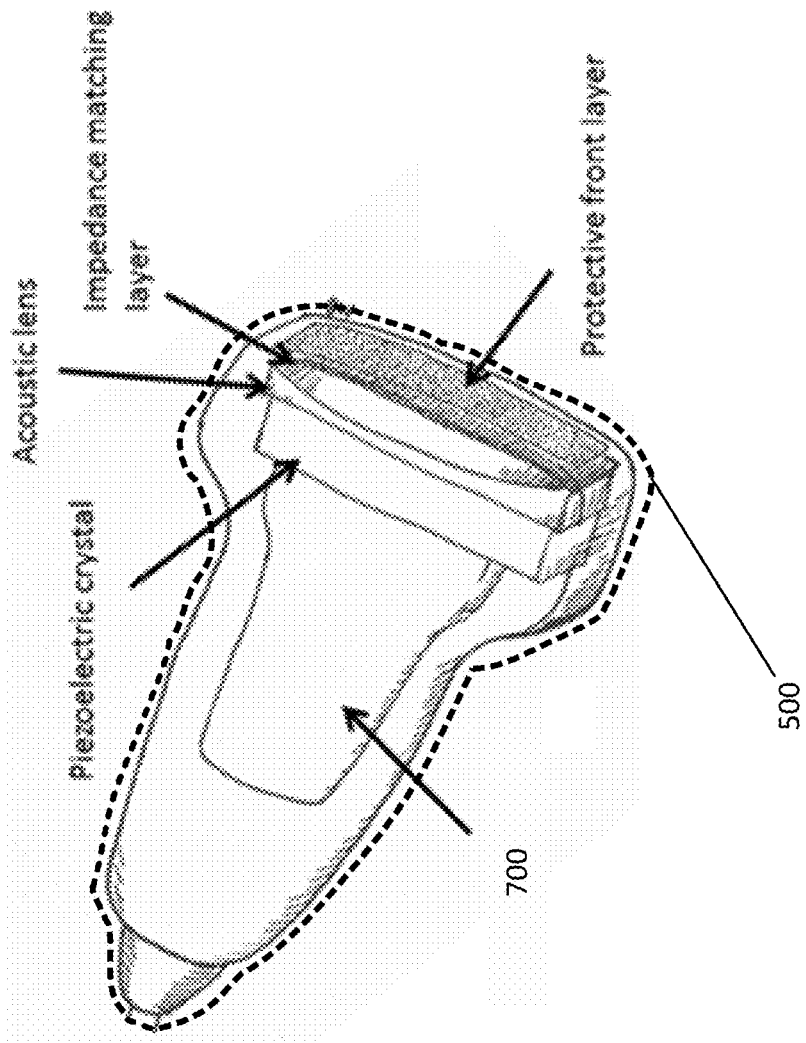
FIG. 17 shows embodiments of the sterile drapes being used with other medical devices.

The sterile drape (or sterile barrier) can be used with other medical devices that need to be maintained sterile. Examples of other medical devices with which the sterile drape may be used includes ultrasound devices, smaller CT scanners currently under development, and even a tablet, portable computer, or a similar kind of information device that might be used by the medical personnel. An example of the sterile drape 500 being used with a wireless ultrasound wand 700 is illustrated in FIG. 17 where the sterile drape 500 is shown with a dashed line around the wand 700. In FIG. 17, the sterile drape is shown in its closed position with the open end already closed.

The medical devices described herein can be used to treat any type of patient. So while they are described to be used with human patients, they can also be used with animals in veterinary procedures. As well, some of the medical devices—such as the x-ray devices—could be used in dental procedures.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A sterile drape for a medical device, wherein the medical device comprises a C-shaped support arm, the sterile drape comprising:
a closed end portion;
a middle portion with a size sufficient to enclose a part of the medical device being used near a patient; and
an open end portion, the end portion configured to be closed by connecting the open end portion to itself once the middle portion encloses the part of the medical device being used near a patient;
wherein the sterile drape creates a sterile barrier around the entire medical device once the open end is closed.

2. The sterile drape of claim 1, wherein the medical device is a hand-held or self-supported x-ray device.

3. The sterile drape of claim 2, wherein the medical device is configured to be self-contained and operate without using external cables or wires.

4. The sterile drape of claim 2, wherein the sterile drape is sufficiently flexible so that no opening or breaks occur as the location of an X-ray source and an X-ray detector change relative to each other.

5. The sterile drape of claim 1, wherein the sterile barrier is made of plastic, a breathable fabric, or a combination thereof.

6. The sterile drape of claim 1, wherein the medical device is operable while enclosed in the sterile drape.

7. The sterile drape of claim 1, wherein the sterile drape comprises a single sheet of material.

8. The sterile drape of claim 1, further comprising a pocket located adjacent a handhold or adjustment handle in the medical device.

9. The sterile drape of claim 1, wherein a protective shield or additional barrier is incorporated into the sterile drape.

10. A hand-held or self-supported X-ray device, comprising:
a C-shaped support arm;
an X-ray source contained near one end of the support arm;
an X-ray detector contained near the other end of the support arm; and
a sterile drape enclosing the X-ray source, the X-ray detector, and the support arm, the sterile drape comprising:
a closed end portion;
a middle portion with a size sufficient to enclose a part of the x-ray device being used near a patient; and
an open end portion configured to be closed by connecting the open end portion to itself once the middle portion encloses the part of the x-ray device;
wherein the sterile drape creates a sterile barrier around the entire x-ray device once the open end is closed.

11. The device of claim 10, wherein the x-ray device is configured to be self-contained and operate without using external cables or wires.

12. The device of claim 10, wherein the sterile drape is made of plastic, a breathable fabric, or a combination thereof.

13. The device of claim 10, wherein the sterile drape is sufficiently flexible so that no opening or breaks occur as the location of the X-ray source and X-ray detector change relative to each other.

14. The device of claim 10, wherein the x-ray device is operable while enclosed in the sterile barrier.

15. The device of claim 10, wherein the sterile drape comprises a single sheet of material.

16. The device of claim 15, wherein the sterile drape comprises a pocket located adjacent a handhold or adjustment handle in the support arm of the x-ray device.

17. A hand-held or self-supported X-ray device, comprising:
a C-shaped support arm;
an X-ray source contained near one end of the support arm;
an X-ray detector contained near the other end of the support arm; and
a sterile drape enclosing the X-ray source, the X-ray detector, and the support arm without any breaks and maintain a sterile surgical field; the sterile drape comprising:
a closed end portion;
a middle portion with a size sufficient to enclose a part of the x-ray device; and
an open end portion configured to be closed by connecting the open end portion to itself once the middle portion encloses the part of the x-ray device;
wherein the x-ray device is configured to be self-contained and operate without using external cables or wires.

18. The device of claim 17, wherein the x-ray device is operable while enclosed in the sterile barrier.

* * * * *